United States Patent
Jarjour et al.

(10) Patent No.: US 12,404,500 B2
(45) Date of Patent: Sep. 2, 2025

(54) HOMING ENDONUCLEASE VARIANTS

(71) Applicant: Novo Nordisk A/S, Bagsværd (DK)

(72) Inventors: Jordan Jarjour, Seattle, WA (US);
Kyle Havens, Seattle, WA (US);
Constantine Chrysostomou, Fairfax, VA (US)

(73) Assignee: NOVO NORDISK A/S, Bagsværd (DK)

( * ) Notice: Subject to any disclaimer, the term of this patent is extended or adjusted under 35 U.S.C. 154(b) by 779 days.

(21) Appl. No.: 17/311,464

(22) PCT Filed: Dec. 9, 2019

(86) PCT No.: PCT/US2019/065211
§ 371 (c)(1),
(2) Date: Jun. 7, 2021

(87) PCT Pub. No.: WO2020/123371
PCT Pub. Date: Jun. 18, 2020

(65) Prior Publication Data
US 2022/0119784 A1  Apr. 21, 2022

Related U.S. Application Data

(60) Provisional application No. 62/777,476, filed on Dec. 10, 2018.

(51) Int. Cl.
*C12N 9/22* (2006.01)

(52) U.S. Cl.
CPC ............ *C12N 9/22* (2013.01); *C07K 2319/80* (2013.01)

(58) Field of Classification Search
CPC .............................. C12N 9/22; C07K 2319/80
See application file for complete search history.

(56) References Cited

U.S. PATENT DOCUMENTS

| | | | |
|---|---|---|---|
| 4,751,180 A | 6/1988 | Cousens et al. |
| 4,873,192 A | 10/1989 | Kunkel |
| 4,935,233 A | 6/1990 | Bell et al. |
| 5,804,413 A | 9/1998 | DeLuca |
| 5,837,532 A | 11/1998 | Preston et al. |

(Continued)

FOREIGN PATENT DOCUMENTS

| | | |
|---|---|---|
| CN | 101679959 A | 3/2010 |
| CN | 106749666 A | 5/2017 |

(Continued)

OTHER PUBLICATIONS

Sethuraman, J., et al. "Genes within genes: multiple LAGLIDADG homing endonucleases target the ribosomal protein S3 gene encoded within an rnl group I intron of Ophiostoma and related taxa." Molecular biology and evolution 26.10 (2009): 2299-2315. (Year: 2009).*

(Continued)

*Primary Examiner* — Louise W Humphrey
*Assistant Examiner* — Candice Lee Swift
(74) *Attorney, Agent, or Firm* — Panitch Schwarze Belisario & Nadel LLP; Stephany G. Small; Travis W. Bliss

(57) ABSTRACT

The present disclosure provides homing endonuclease variants and megaTALs reprogrammed to bind and cleave a polynucleotide sequence in the genome. The homing endonuclease variants and megaTALs have been engineered to increase the thermostability and/or activity.

20 Claims, 7 Drawing Sheets

Specification includes a Sequence Listing.

(56) References Cited

U.S. PATENT DOCUMENTS

| | | | |
|---|---|---|---|
| 5,846,782 | A | 12/1998 | Wickham et al. |
| 5,994,136 | A | 11/1999 | Naldini et al. |
| 6,013,516 | A | 1/2000 | Verma et al. |
| 6,649,595 | B2 | 11/2003 | Clackson et al. |
| 6,682,907 | B1 | 1/2004 | Charneau et al. |
| 6,692,736 | B2 | 2/2004 | Yu et al. |
| 8,614,092 | B2 | 12/2013 | Zhang et al. |
| 8,735,553 | B1 | 5/2014 | Li et al. |
| 8,784,799 | B2 | 7/2014 | Samulski et al. |
| 8,809,058 | B2 | 8/2014 | Ferrari et al. |
| 8,889,641 | B2 | 11/2014 | Asokan et al. |
| 9,012,224 | B2 | 4/2015 | Bowles et al. |
| 9,017,967 | B2 | 4/2015 | Bonas et al. |
| 9,169,492 | B2 | 10/2015 | Monahan et al. |
| 9,169,494 | B2 | 10/2015 | Hewitt et al. |
| 9,506,120 | B2 | 11/2016 | Doyon et al. |
| 11,345,754 | B2 | 5/2022 | Hu et al. |
| 11,779,654 | B2 * | 10/2023 | Jarjour .................. C12N 9/6454 435/463 |
| 2011/0256607 | A1 | 10/2011 | Hausner et al. |
| 2013/0337454 | A1 | 12/2013 | Duchateau et al. |
| 2014/0148361 | A1 | 5/2014 | Stoddard et al. |
| 2015/0266973 | A1 | 9/2015 | Jarjour et al. |
| 2016/0102323 | A1 | 4/2016 | Jarjour et al. |
| 2016/0130569 | A1 | 5/2016 | Jarjour et al. |
| 2017/0298329 | A1 | 10/2017 | Takeuchi et al. |
| 2021/0040165 | A1 | 2/2021 | Mann et al. |

FOREIGN PATENT DOCUMENTS

| | | |
|---|---|---|
| CN | 106939049 A | 7/2017 |
| EA | 201492222 A1 | 5/2015 |
| EP | 2215223 B1 | 8/2010 |
| IN | 201617011596 | 11/2021 |
| JP | 2010539929 A | 12/2010 |
| JP | 2016520308 A | 7/2016 |
| WO | 9102788 A1 | 3/1991 |
| WO | 9604394 A1 | 2/1996 |
| WO | 9815637 A1 | 4/1998 |
| WO | 9906583 A1 | 2/1999 |
| WO | 2006010834 A1 | 2/2006 |
| WO | 2007049095 A1 | 5/2007 |
| WO | 2011156430 A2 | 12/2011 |
| WO | 2012068380 A2 | 5/2012 |
| WO | 2012118717 A2 | 9/2012 |
| WO | 2013126794 A1 | 8/2013 |
| WO | 201414744 A1 | 1/2014 |
| WO | 2014184741 A1 | 11/2014 |
| WO | 2014184744 A1 | 11/2014 |
| WO | 2014191525 A1 | 12/2014 |
| WO | 2014191527 A1 | 12/2014 |
| WO | 2015017214 A1 | 2/2015 |
| WO | 2017156484 A1 | 9/2017 |
| WO | 2017177137 A1 | 10/2017 |
| WO | 2018022619 A1 | 2/2018 |
| WO | 2018035141 A1 | 2/2018 |
| WO | 2018035423 A1 | 2/2018 |
| WO | 2018039333 A1 | 3/2018 |
| WO | 2018049226 A1 | 3/2018 |
| WO | 2018071565 A1 | 4/2018 |
| WO | 2018075541 A1 | 4/2018 |
| WO | 2018218194 A1 | 11/2018 |
| WO | 2020123375 A1 | 11/2018 |
| WO | WO-2020072059 A1 * | 4/2020 ......... A61K 39/0011 |

OTHER PUBLICATIONS

Takeuchi, Ryo, et al. "Tapping natural reservoirs of homing endonucleases for targeted gene modification." Proceedings of the National Academy of Sciences 108.32 (2011): 13077-13082. (Year: 2011).*

Kay et al., "A Bacterial Effector Acts as a Plant Transcription Factor and Induces a Cell Size Regulator," Science, vol. 318, No. 5850, pp. 648-651 (Oct. 26, 2007).

Kay, J.E., "Structure-function relationships in the FK506-binding protein (FKBP) family of peptidylprolyl cis-trans somerases," Biochem J., vol. 314 (Pt 2), pp. 361-385 (1996).

Kim et al., "Hybrid restriction enzymes: zinc finger fusions to Fok I cleavage domain," Proceedings of the National Academy of Sciences, vol. 93, No. 3, pp. 1156-1160 (1996).

Kozak, M., "An analysis of 5'-noncoding sequences from 699 vertebrate messenger RNAs," Nucleic Acids Research, vol. 15, No. 20, pp. 8125-8148 (1987).

Kozak, M., "Point Mutations Define a Sequence Flanking the AUG Initiator Codon That Modulates Translation by Eukaryotic Ribosomes," Cell, vol. 44, No. 2, pp. 283-292 (1986).

Kunkel, et al., "Rapid and Efficient Site-Specific Mutagenesis Without Phenotypic Selection," Methods in Enzymology, vol. 154, pp. 367-382 (1987).

Kunkel, T.A., "Rapid and efficient site-specific mutagenesis without phenotypic selection," Proc. Natl. Acad. Sci. USA, vol. 82, No. 2, pp. 488-492 (1985).

Kutner et al., "Production, concentration and titration of pseudotyped HIV-1-based lentiviral vectors," Nature Protocols, vol. 4, No. 4, pp. 495-505 (2009).

Kutner et al., "Simplified production and concentration of HIV-1-based lentiviral vectors using HYPERFlask vessels and anion exchange membrane chromatography," BMC Biotechnology, vol. 9, No. 10, pp. 1-7 (2009).

Lai et al., "Long-Term Evaluation of AAV-Mediated sFlt-1 Gene Therapy for Ocular Neovascularization in Mice and Monkeys," Molecular Therapy, vol. 12, No. 4, pp. 659-668 (2005).

Le Gal La Salle et al., "An Adenovirus Vector for Gene Transfer into Neurons and Glia in the Brain," Science, vol. 259, pp. 988-990 (1993).

Levrero et al., "Defective and nondefective adenovirus vectors for expressing foreign genes in vitro and in vivo," Gene, vol. 101, pp. 195-202 (1991).

Liu et al., "Design of polydactyl zinc-finger proteins for unique addressing within complex genomes, " Proceedings of the National Academy of Sciences USA, vol. 94, No. 11, pp. 5525-5530 (1997).

Liu et al., "HnRNP L binds a cis-acting RNA sequence element that enables intron-dependent gene expression," Genes & Development, vol. 9, pp. 1766-1780 (1995).

Liu et al., "Poly(cationic lipid)-mediated in vivo gene delivery to mouse liver," Gene Therapy, vol. 10, No. 2, pp. 180-187 (2003).

Maratea et al., "Deletion and fusion analysis of the phage phi X174 lysis gene E," Gene, vol. 40, No. 1, pp. 39-46 (1985).

McMurrough et al., "Control of catalytic efficiency by a coevolving network of catalytic and noncatalytic residues," PNAS, pp. E2376-E2383 (2014).

Murphy et al., "Genetic construction, expression, and melanoma-selective cytotoxicity of a diphtheria toxin-related alpha-melanocyte-stimulating hormone fusion protein," Proc. Natl. Acad. Sci. U S A., vol. 83, No. 21, pp. 8258-8262 (Nov. 1986).

Nakayama et al., "Structure of a Hyperthermophilic Archael Homing Endonuclease, I-Tsp061I: Contribution of Cross-domain Polar Networks to Thermostability," Journal of Molecular Biology, vol. 365, pp. 362-378 (2007).

Naldini et al., "Efficient transfer, integration, and sustained long-term expression of the transgene in adult rat brains injected with a lentiviral vector," Proc. Natl. Acad. Sci. USA, vol. 93, No. 21, pp. 11382-11388 (1996).

Naldini et al., "In Vivo Gene Delivery and Stable Transduction of Nondividing Cells by a Lentiviral Vector," Science, vol. 272, No. 5259, pp. 263-267 (1996).

Naldini, L., "Lentiviruses as gene transfer agents for delivery to non-dividing cells," Current Opinion in Biotechnology, vol. 9, pp. 457-463 (1998).

Pâques et al., "Meganucleases and DNA Double-Strand Break-Induced Recombination: Perspectives for Gene Therapy," Current Gene Therapy, vol. 7, pp. 49-66 (2007).

(56) References Cited

OTHER PUBLICATIONS

Patel et al., "Impact of chimeric immune receptor extracellular protein domains on T cell function," Gene Therapy, vol. 6, No. 3, pp. 412-419 (1999).
Platten et al., "Tryptophan Catabolismin Cancer: Beyond IDO and Tryptophan Depletion," Cancer Research, vol. 72, No. 21, pp. 5435-5440 (2012).
Pomerantz et al., "Analysis of homeodomain function by structure-based design of a transcription factor," Proc. Natl. Acad. Sci. USA, vol. 92, No. 21, pp. 9752-9756 (1995).
Pomerantz et al., "Structure-Based Design of Transcription Factors," Science, vol. 267, pp. 93-96 (1995).
Ragot et al., "Efficient adenovirus-mediated transfer of a human minidystrophin gene to skeletal muscle of mdx mice," Nature, vol. 361, pp. 647-650 (1993).
Reich et al., "Efficient Trans-Splicing in the Retina Expands the Utility of Adeno-Associated Virus as a Vector for Gene Therapy," Human Gene Therapy, vol. 14, No. 1, pp. 37-44 (2003).
Rosenfeld et al., "Adenovirus-Mediated Transfer of a Recombinant alpha1-Antitrypsin Gene to the Lung Epithelium in Vivo," Science, vol. 252, pp. 431-434 (1991).
Rosenfeld et al., "In Vivo Transfer of the Human Cystic Fibrosis Transmembrane Conductance Regulator Gene to the Airway Epithelium," Cell, vol. 68, pp. 143-155 (1992).
Ryan et al., "Virus-encoded proteinases of the picornavirus supergroup," Journal of General Virology, vol. 78 (Pt 4), pp. 699-723 (1997).
Sather et al., "Efficient modification of CCR5 in primary human hematopoietic cells using a megaTAL nuclease and AAV donor template," Sci. Transl Med., vol. 7, No. 307, pp. 1-14 (2015).
Standaert et al., "Molecular cloning and overexpression of the human FK506-binding protein FKBP," Nature, vol. 346, No. 6285, pp. 671-674 (1990).
Sterman et al., "Adenovirus-Mediated Herpes Simplex Virus Thymidine Kinase/Ganciclovir Gene Therapy in Patients with Localized Malignancy: Results of a Phase I Clinical Trial in Malignant Mesothelioma," Human Gene Therapy, vol. 9, No. 7, pp. 1083-1092 (1998).
Stoddard et al., "Homing Endonucleases: From Microbial Genetic Invaders to Reagents for Targeted DNA Modification," Structure, vol. 19, pp. 7-15 (Jan. 12, 2011).
Stoddard, "Homing endonuclease structure and function," Quarterly Reviews of Biophysics, vol. 38, No. 1, pp. 49-95 (2005).
Szymczak et al., "Correction of multi-gene deficiency in vivo using a single 'self-cleaving' 2A peptide-based retroviral vector," Nature Biotechnology, vol. 22, No. 5, pp. 589-594 (2004).
Takeuchi et al., "Engineering of customized meganucleases via in vitro compartmentalization and in cellulo optimization," Methods Mol. Biol., vol. 1239, pp. 105-132 (2015).
Takeuchi et al., "Tapping natural reservoirs of homing endonucleases for targeted gene modification," Proceedings of the National Academy of Sciences, National Academy of Sciences, vol. 108, No. 32, pp. 13077-13082 (2011).
Yan et al., "Trans-splicing vectors expand the utility of adeno-associated virus for gene therapy," PNAS, vol. 97, No. 12, pp. 6716-6721 (2000).
Zennou et al., "HIV-1 Genome Nuclear Import is Mediated by a Central DNA Flap," Cell, vol. 101, No. 2, pp. 173-185 (2000).
Zhong et al., "Chimeric antigen receptors combining 4-1BB and CD28 signaling domains augment PI3kinase/AKT/Bcl-XL activation and CD8+ T cell-mediated tumor eradication," Molecular Therapy, vol. 18, No. 2, pp. 413-420 (2010).
Zufferey et al., "Multiply attenuated lentiviral vector achieves efficient gene delivery in vivo," Nat. Biotechnol., vol. 15, No. 9, pp. 871-875 (1997).
Zufferey et al., "Woodchuck hepatitis virus posttranscriptional regulatory element enhances expression of transgenes delivered by retroviral vectors," Journal of Virology, vol. 73, No. 4, pp. 2886-2892 (1999).
Challita et al., "Multiple Modifications in cis Elements of the Long Terminal Repeat of Retroviral Vectors Lead to Increased Expression and Decreased DNA Methylation in Embryonic Carcinoma Cells," Journal of Virology, vol. 69, No. 2, pp. 748-755 (1995).
Ashworth et al., "Computational redesign of endonuclease DNA binding and cleavage specificity," Nature, vol. 441, No. 7093, pp. 656-659 (Jun. 1, 2006).
Balazs et al., "Liposomes for Use in Gene Delivery," Journal of Drug Delivery, vol. 2011, pp. 1-12 (2011).
Baxter et al., "Engineering domain fusion chimeras from I-Onul family LAGLIDADG homing endonucleases," Nucleic Acids Research, vol. 40, No. 16, pp. 7985-8000 (2012).
Belfort et al., "Homing Endonucleases: From Genetic Anomalies to Programmable Genomic Clippers," Methods in Molecular Biology, vol. 1123, pp. 1-26 (2014).
Bennardo et al., "Limiting the Persistence of a Chromosome Break Diminishes Its Mutagenic Potential," PLoS Genetics, vol. 5, No. 10:e1000683, pp. 1-14 (Oct. 2009).
Bird et al., "Single-chain antigen-binding proteins," Science, vol. 242, No. 4877, pp. 423-427 (1988).
Boissel et al., "megaTALS: a rare-cleaving nuclease architecture for therapeutic genome engineering," Nucleic Acids Research, vol. 42, No. 4, pp. 2591-2601 (2014).
Brinkman et al., "Easy quantitative assessment of genome editing by sequence trace decomposition," Nucleic Acids Research, vol. 42, No. 22, e168, pp. 1-8 (2014).
Brown et al., "A mammalian protein targeted by G1-arresting rapamycin-receptor complex," Nature, vol. 369, No. 6483, pp. 756-758 (1994).
Brunner et al., "Cytotoxic T cells: Double-barreled shot guns," Nature Medicine, vol. 5, No. 1, 1 page (Jan. 1999).
Certo et al., "Coupling endonucleases with DNA end-processing enzymes to drive gene disruption," Nat. Methods, vol. 9, No. 10, pp. 973-975 (Oct. 2012).
Certo et al., "Tracking genome engineering outcome at individual DNA breakpoints," Nat Methods, vol. 8, No. 8, pp. 671-676 (2012).
Chaudhary et al., "A rapid method of cloning functional variable-region antibody genes in *Escherichia coli* as single-chain immunotoxins," Proceedings of the National Academy of Sciences, vol. 87, No. 3, pp. 1066-1070 (and correction) (1990).
Chevalier et al., "Design, Activity, and Structure of a Highly Specific Artificial Endonuclease," Molecular Cell, vol. 10, pp. 895-905 (Oct. 2002).
Clever et al., "RNA Secondary Structure and Binding Sites for gag Gene Products in the 5' Packaging Signal of Human Immunodeficiency Virus Type 1," Journal of Virology, vol. 69, No. 4, pp. 2101-2109 (1995).
Cullen et al., "Regulatory Pathways Governing HIV-1 Replication", Cell, vol. 58, pp. 423-426 (1989).
Cullen, B.R., "Human Immunodeficiency Virus as a Prototypic Complex Retrovirus," Journal of Virology, vol. 65, No. 3, pp. 1053-1056 (1991).
Database Geneseq [Online] Oct. 24, 2013 (Oct. 24, 2013), "I-Onul homing endonuclease, SEQ 15," XP002798406, retrieved from EBI accession No. GSP:BAS88181 Database accession No. BAS88181 *sequence *.
Dayhoff et al., "A model of evolutionary change in proteins. In: Atlas of Protein Sequence and Structure," M.O. Dayhoff, ed., National Biomedical Research Foundation, Washington, DC., pp. 345-358 (1978).
De Felipe et al., "Targeting of Proteins Derived from Self-Processing Polyproteins Containing Multiple Signal Sequences," Traffic, vol. 5, No. 8, pp. 616-626 (2004).
Desjarlais et al., "Length-encoded multiplex binding site determination: application to zinc finger proteins," Proceedings of the National Academy of Sciences, vol. 91, No. 23, pp. 11099-11103 (1994).
Desjarlais et al., "Use of a zinc-finger consensus sequence framework and specificity rules to design specific DNA binding proteins," Proceedings of the National Academy of Sciences, vol. 90, No. 6, pp. 2256-2260 (1993).
Donnelly et al., "The 'cleavage' activities of foot-and-mouth disease virus 2A site-directed mutants and naturally occurring '2A-like' sequences," Journal of General Virology, vol. 82 (Pt 5), pp. 1027-1041 (2001).

(56) References Cited

OTHER PUBLICATIONS

Duan et al., "Expanding AAV Packaging Capacity with Trans-splicing or Overlapping Vectors: A Quantitative Comparison," Molecular Therapy, vol. 4, No. 4, pp. 383-391 (2001).
Duke et al., "Sequence and Structural Elements That Contribute to Efficient Encephalomyocarditis Virus RNA Translation," Journal of Virology, vol. 66, No. 3, pp. 1602-1609 (1992).
Dull et al., "A Third-Generation Lentivirus Vector with a Conditional Packaging System," Journal of Virology, vol. 72, No. 11, pp. 8463-8671 (1998).
Epinat et al., "A novel engineered meganuclease induces homologous recombination in yeast and mammalian cells," Nucleic Acids Research, vol. 31, No. 11, pp. 2952-2962 (2003).
Extended European Search Report issued Jun. 15, 2020 in EP Application No. 17849655.0.
GenBank Accession No. AAA58476.1, "FK506-binding protein 12 [*Homo sapiens*]," Jun. 10, 2016, 2 pages.
GenBank Accession No. L34075.1, "Human FKBP-rapamycin associated protein (FRAP) mRNA, complete cds," Dec. 31, 1994, 4 pages.
Ghosh et al., "A Hybrid Vector System Expands Adeno-associated Viral Vector Packaging Capacity in a Transgene-Independent Manner," Molecular Therapy. vol. 16, No. 1, pp. 124-130 (2008).
Ghosh et al., "Efficient Transgene Reconstitution with Hybrid Dual AAV Vectors Carrying the Minimized Bridging Sequences," Human Gene Therapy, vol. 22, No. 1, pp. 77-83 (2011).
Ghosh et al., "Viral serotype and the transgene sequence influence overlapping adeno- associated viral (AAV) vector-mediated gene transfer in skeletal muscle," J. Gene Med., vol. 8, No. 3, pp. 298-305 (2006).
Gomez-Foix et al., "Adenovirus-mediated Transfer of the Muscle Glycogen Phosphorylase Gene into Hepatocytes Confers Altered Regulation of Glycogen Metabolism," J. Biol. Chem., vol. 267, No. 35, pp. 25129-25134 (Dec. 15, 1992).
Graham et al., "Adenovirus-Based Expression Vectors and Recombinant Vaccines," Vaccines: New Approaches to Immunological Problems, Chapter 16, pp. 363-390 (1992).
Graham et al., "Characteristics of a Human Cell Line Transformed by DNA from Human Adenovirus Type 5," J. Gen. Virol., vol. 36, pp. 59-72 (1977).
Graham et al., "Manipulation of Adenovirus Vectors," Methods in Molecular Biology, vol. 7: Gene Transfer and Expression Protocols, Chapter 11, pp. 109-129 (1991).
Grunhaus et al., "Adenoviruses as cloning vectors," Semin. Virol., vol. 3, pp. 237-252 (1992).
Hensgens et al., "Two Intron Sequences in Yeast Mitochondrial COX1 Gene: Homology among URF-Containing Introns and Strain-Dependent Variation in Flanking Exons," Cell, vol. 32, pp. 379-389 (Feb. 1983).
Herz et al., "Adenovirus-mediated transfer of low density lipoprotein receptor gene acutely accelerates cholesterol clearance in normal mice," PNAS USA, vol. 90, pp. 2812-2816 (1993).
Huang et al., "Role of the Hepatitis B Virus Posttranscriptional Regulatory Element in Export of Intronless Transcripts," Molecular and Cellular Biology, vol. 15, No. 7, pp. 3864-3869 (1995).
Huez et al., "Two Independent Internal Ribosome Entry Sites Are Involved in Translation Initiation of Vascular Endothelial Growth Factor mRNA," Molecular and Cellular Biology, vol. 18, No. 11, pp. 6178-6190 (Nov. 1998).
International Search Report and Written Opinion issued Mar. 4, 2020 in International Application No. PCT/US2019/065223.
International Search Report and Written Opinion issued Jul. 20, 2020 in International Application No. PCT/US2019/065211.
International Search Report and Written Opinion issued Nov. 16, 2017 in International Application No. PCT/US2017/050774.
Irion et al., "Identification and targeting of the ROSA26 locus in human embryonic stem cells," Nature Biotechnology, vol. 25, No. 12, pp. 1477-1482 (2007).
Jackson et al., "Internal initiation of translation in eukaryotes: the picornavirus paradigm and beyond," RNA, vol. 1, No. 10, pp. 985-1000 (1995).
Jackson et al., "The novel mechanism of initiation of picornavirus RNA translation," Trends Biochem. Sci., vol. 15, No. 12, pp. 477-483 (1990).
Jarjour et al., "High-resolution profiling of homing endonuclease binding and catalytic specificity using yeast surface display," Nucleic Acids Research, vol. 37, No. 20, pp. 6871-6880 (2009).
Jones et al., "Isolation of Deletion and Substitution Mutants of Adenovirus Type 5," Cell, vol. 13, pp. 181-188 (1978).
Chan et al., The Design and In Vivo Evaluation of Engineered I-OnuIBased Enzymes for HEG Gene Drive, 8(9) Plos One 1-5 (Sep. 2013).
Cox et al., Therapeutic genome editing: prospects and challenges, 21(2) Nature Medicine 121-131 (2015).
Zhang et al., Research progress in engineered nucleases for genome site-specific editing, 33(12) Basic & Clinical Medicine 1634-1637 (Dec. 2013) (English abstract).
GenPept 6BD0_A, Chain A, Ribosomal protein 3/homing endonuclease-like protein fusion (available through NCBI; disclosed by Brown, C., Zhang, K., Laforet, M., McMurrough, T.A., Gloor, G.B., Edgell, D.R.and Junop, M. in 2017) 2 pages (Mar. 13, 2024).
Lambert et al., "Indirect DNA sequence recognition and its impact on nuclease cleavage activity," Structure 24(6): 862-873 (Jun. 7, 2016).

* cited by examiner

HOMING ENDONUCLEASE VARIANTS

CROSS REFERENCE TO RELATED APPLICATIONS

This application claims the benefit under 35 U.S.C. § 119 (e) of U.S. Provisional Application No. 62/777,476, filed Dec. 10, 2018, which is incorporated by reference herein in its entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is BLUE_110_Correctd.txt. The text file is 84, 108 bytes, was created on May 19, 2024, and is being submitted electronically.

BACKGROUND

Technical Field

The present disclosure relates to genome editing compositions with improved stability and activity. More particularly, the disclosure relates to nuclease variants with improved stability and/or activity, compositions, and methods of making and using the same for genome editing.

Description of the Related Art

Mutations in 3000 human genes have already been linked to disease phenotypes (omim.org), and more disease relevant genetic variations are being uncovered at a staggeringly rapid pace, many of which are associated with monogenetic diseases or cancer. Genome editing strategies based on programmable nucleases such as meganucleases, zinc finger nucleases, transcription activator-like effector nucleases and the clustered regularly interspaced short palindromic repeat (CRISPR)-associated nuclease Cas9 hold tremendous, but as yet unrealized, potential for the treatment of diseases, disorders, and conditions with a genetic component. Particular obstacles to implementing nuclease-based genome editing tools as therapeutic strategies include, but are not limited to low genome editing efficiencies, nuclease specificity, nuclease stability, and delivery challenges. The current state of the art for most genome editing strategies fails to meet some or all of these criteria.

BRIEF SUMMARY

The present disclosure generally relates, in part, to compositions comprising homing endonuclease (HE) variants and megaTALs with improved stability and activity that cleave a target site in the human genome and methods of using the same. In particular embodiments, the HE variants and megaTALs are engineered to improve or enhance the thermostability of the enzyme and/or improve the catalytic activity of the enzyme.

In various embodiments, the present disclosure contemplates, in part, a polypeptide comprising an engineered homing endonuclease that has been engineered to improve stability and binding and cleavage of a target site.

In various embodiments, an I-OnuI homing endonuclease (HE) variant comprises one or more amino acid substitutions relative to a parent I-OnuI HE comprising the amino acid sequence set forth in SEQ ID NO: 1, wherein the one or more amino acid substitutions increase the thermostability of the I-OnuI HE variant compared to the parent I-OnuI HE.

In certain embodiments, the one or more amino acid substitutions is at an amino acid position selected from the group consisting of: 114, A19, V116, F168, D208, N246, and L263.

In certain embodiments, the amino acid substitutions are at the following amino acid positions: 114, A19, F168, D208, and N246.

In some embodiments, the one or more amino acid substitutions is at an amino acid position selected from the group consisting of: K108, K156, S176, E231, V261, E277, and G300.

In some embodiments, the one or more amino acid substitutions is at an amino acid position selected from the group consisting of: N31, N33, K52, Y97, K124, K147, I153, K209, E264, and D268.

In particular embodiments, an I-OnuI HE variant comprises three or more amino acid substitutions is at an amino acid position selected from the group consisting of: I14, A19, K108, V116, K156, F168, S176, D208, E231, N246, V261, L263, E277, and G300.

In particular embodiments, an I-OnuI HE variant comprises three or more amino acid substitutions is at an amino acid position selected from the group consisting of: I14, A19, K108, V116, K156, F168, S176, D208, E231, N246, V261, L263, E277, and G300; and one or more amino acid substitutions is at an amino acid position selected from the group consisting of: N31, N33, K52, Y97, K124, K147, I153, K209, E264, and D268.

In further embodiments, the I-OnuI HE variant comprises five or more amino acid substitutions is at an amino acid position selected from the group consisting of: I14, A19, K108, V116, K156, F168, S176, D208, E231, N246, V261, L263, E277, and G300.

In certain embodiments, an I-OnuI HE variant comprises five or more amino acid substitutions is at an amino acid position selected from the group consisting of: I14, A19, K108, V116, K156, F168, S176, D208, E231, N246, V261, L263, E277, and G300; and one or more amino acid substitutions is at an amino acid position selected from the group consisting of: N31, N33, K52, Y97, K124, K147, I153, K209, E264, and D268.

In particular embodiments, an I-OnuI HE variant has a $TM_{50}$ at least 10° C. higher than the $TM_{50}$ of the parent I-OnuI HE.

In some embodiments, an I-OnuI HE variant has a $TM_{50}$ at least 15° C. higher than the $TM_{50}$ of the parent I-OnuI HE.

In certain embodiments, an I-OnuI HE variant has a $TM_{50}$ at least 20° C. higher than the $TM_{50}$ of the parent I-OnuI HE.

In certain embodiments, an I-OnuI HE variant has a $TM_{50}$ at least 25° C. higher than the $TM_{50}$ of the parent I-OnuI HE.

In particular embodiments, an I-OnuI HE variant targets a site in a gene selected from the group consisting of: HBA, HBB, HBG1, HBG2, BCL11A, PCSK9, TCRA, TCRB, B2M, HLA-A, HLA-B, HLA-C, HLA-E, HLA-F, HLA-G, CIITA, AHR, PD-1, CTLA4, TIGIT, TGFβR2, LAG-3, TIM-3, BTLA, IL4R, IL6R, CXCR1, CXCR2, IL10R, IL13Rα2, TRAILR1, RCAS1R, and FAS.

In various embodiments, an I-OnuI homing endonuclease (HE) variant comprising one or more amino acid substitutions relative to a parent I-OnuI HE sequence, wherein the one or more amino acid substitutions increase the thermostability of the I-OnuI HE variant compared to the parent I-OnuI HE.

In further embodiments, a parent I-OnuI HE amino acid sequence set is forth in SEQ ID NO: 1.

In further embodiments, the one or more amino acid substitutions is at an amino acid position selected from the group consisting of: I14, A19, V116, F168, D208, N246, and L263.

In certain embodiments, the amino acid substitutions are at the following amino acid positions: I14, A19, F168, D208, and N246.

In certain embodiments, the amino acid substituted for I14 is selected from the group consisting of: S, N, M, K, F, D, T, and V.

In some embodiments, the amino acid substituted for I14 is selected from the group consisting of: T and V.

In particular embodiments, the amino acid substituted for A19 is selected from the group consisting of: C, D, I, L, S, T and V.

In additional embodiments, the amino acid substituted for A19 is selected from the group consisting of: T and V.

In certain embodiments, the amino acid substituted for V116 is selected from the group consisting of: F, D, A, L and I.

In particular embodiments, the amino acid substituted for V116 is selected from the group consisting of: L and I.

In certain embodiments, the amino acid substituted for F168 is selected from the group consisting of: H, Y, I, V, P, L and S.

In additional embodiments, the amino acid substituted for F168 is selected from the group consisting of: L and S.

In some embodiments, the amino acid substituted for D208 is selected from the group consisting of: N, V, Y, and E.

In particular embodiments, the amino acid substituted for D208 is E.

In particular embodiments, the amino acid substituted for N246 is selected from the group consisting of: H, I, D, R, S, T, V, Y, and K.

In particular embodiments, the amino acid substituted for N246 is K.

In additional embodiments, the amino acid substituted for L263 is selected from the group consisting of: H, F, P, T, V, and R.

In further embodiments, the amino acid substituted for L263 is R.

In additional embodiments, the one or more amino acid substitutions is at an amino acid position selected from the group consisting of: K108, K156, S176, E231, V261, E277, and G300.

In certain embodiments, the amino acid substituted for K108 is selected from the group consisting of: E, N, Q, R, T, V, and M.

In certain embodiments, the amino acid substituted for K108 is M

In some embodiments, the amino acid substituted for K156 is selected from the group consisting of: N, Q, R, T, V, I, and E.

In particular embodiments, the amino acid substituted for K156 is selected from the group consisting of: I and E In additional embodiments, the amino acid substituted for S176 is selected from the group consisting of: P, N and A.

In further embodiments, the amino acid substituted for S176 is A.

In particular embodiments, the amino acid substituted for E231 is selected from the group consisting of: D, K, V, and G.

In particular embodiments, the amino acid substituted for E231 is selected from the group consisting of: K and G.

In certain embodiments, the amino acid substituted for V261 is selected from the group consisting of: D, G, I, L, S, T, and A.

In some embodiments, the amino acid substituted for V261 is A.

In certain embodiments, the amino acid substituted for E277 is selected from the group consisting of: A, D, G, Q, V, and K.

In additional embodiments, the amino acid substituted for E277 is K.

In further embodiments, the amino acid substituted for G300 is selected from the group consisting of: S, V, D, C, and R.

In particular embodiments, the amino acid substituted for G300 is R.

In additional embodiments, the one or more amino acid substitutions is at an amino acid position selected from the group consisting of: N31, N33, K52, Y97, K124, K147, I153, K209, E264, and D268.

In some embodiments, the amino acid substituted for N31 is selected from the group consisting of: D, H, I, R, K, S, T and Y.

In additional embodiments, the amino acid substituted for N31 is K.

In particular embodiments, the amino acid substituted for N33 is selected from the group consisting of: D, G, H, I, K, S, T and Y.

In particular embodiments, the amino acid substituted for N33 is K.

In certain embodiments, the amino acid substituted for K52 is selected from the group consisting of: Q, R, T, Y, N, E, and M.

In further embodiments, the amino acid substituted for K52 is M.

In particular embodiments, the amino acid substituted for Y97 is selected from the group consisting of: F, N and H.

In other embodiments, the amino acid substituted for Y97 is F.

In particular embodiments, the amino acid substituted for K124 is selected from the group consisting of: E, N, R and T.

In some embodiments, the amino acid substituted for K124 is N.

In particular embodiments, the amino acid substituted for K147 is selected from the group consisting of: E, I, N, R and T.

In certain embodiments, the amino acid substituted for K147 is I.

In further embodiments, the amino acid substituted for I153 is selected from the group consisting of: D, H, K, T, Y, S, V and N.

In other embodiments, the amino acid substituted for I153 is N.

In certain embodiments, the amino acid substituted for K209 is selected from the group consisting of: E, M, N, Q and R.

In particular embodiments, the amino acid substituted for K209 is R.

In additional embodiments, the amino acid substituted for E264 is selected from the group consisting of: A, D, G, K, Q, R and V.

In certain embodiments, the amino acid substituted for E264 is K.

In further embodiments, the amino acid substituted for D268 is selected from the group consisting of: A, E, G, H, N, V and Y.

In particular embodiments, the amino acid substituted for D268 is N.

In particular embodiments, an I-OnuI HE variant comprises three or more amino acid substitutions.

In additional embodiments, the I-OnuI HE variant comprises five or more amino acid substitutions.

In particular embodiments, the I-OnuI HE variant comprises three or more amino acid substitutions is at an amino acid position selected from the group consisting of: I14, A19, K108, V116, K156, F168, S176, D208, E231, N246, V261, L263, E277, and G300.

In further embodiments, an I-OnuI HE variant comprises three or more amino acid substitutions is at an amino acid position selected from the group consisting of: I14, A19, K108, V116, K156, F168, S176, D208, E231, N246, V261, L263, E277, and G300; and one or more amino acid substitutions is at an amino acid position selected from the group consisting of: N31, N33, K52, Y97, K124, K147, I153, K209, E264, and D268.

In some embodiments, an I-OnuI HE variant comprises five or more amino acid substitutions is at an amino acid position selected from the group consisting of: 114, A19, K108, V116, K156, F168, S176, D208, E231, N246, V261, L263, E277, and G300.

In certain embodiments, an I-OnuI HE variant comprises five or more amino acid substitutions is at an amino acid position selected from the group consisting of: I14, A19, K108, V116, K156, F168, S176, D208, E231, N246, V261, L263, E277, and G300; and one or more amino acid substitutions is at an amino acid position selected from the group consisting of: N31, N33, K52, Y97, K124, K147, I153, K209, E264, and D268.

In additional embodiments, an I-OnuI HE variant has a $TM_{50}$ at least 10° C. higher than the TMso of the parent I-OnuI HE.

In particular embodiments, an I-OnuI HE variant has a $TM_{50}$ at least 15° C. higher than the $TM_{50}$ of the parent I-OnuI HE.

In particular embodiments, an I-OnuI HE variant has a $TM_{50}$ at least 20° C. higher than the $TM_{50}$ of the parent I-OnuI HE.

In further embodiments, an I-OnuI HE variant has a $TM_{50}$ at least 25° C. higher than the $TM_{50}$ of the parent I-OnuI HE.

In particular embodiments, an I-OnuI HE variant targets a site in a gene selected from the group consisting of: HBA, HBB, HBG1, HBG2, BCL11A, PCSK9, TCRA, TCRB, B2M, HLA-A, HLA-B, HLA-C, HLA-E, HLA-F, HLA-G, CIITA, AHR, PD-1, CTLA4, TIGIT, TGFβR2, LAG-3, TIM-3, BTLA, IL4R, IL6R, CXCR1, CXCR2, IL10R, IL13Rα2, TRAILR1, RCAS1R, and FAS.

In various embodiments, an I-OnuI homing endonuclease (HE) variant that cleaves a target site in the human BCL11A gene, comprises one or more amino acid substitutions relative to a parent I-OnuI HE sequence, wherein the one or more amino acid substitutions increase the thermostability of the I-OnuI HE variant compared to the parent I-OnuI HE.

In various embodiments, an I-OnuI homing endonuclease (HE) variant that cleaves a target site in the human PCSK9 gene, comprises one or more amino acid substitutions relative to a parent I-OnuI HE sequence, wherein the one or more amino acid substitutions increase the thermostability of the I-OnuI HE variant compared to the parent I-OnuI HE.

In particular embodiments, an I-OnuI homing endonuclease (HE) variant that cleaves a target site in the human PDCD-1 gene, comprises one or more amino acid substitutions relative to a parent I-OnuI HE sequence, wherein the one or more amino acid substitutions increase the thermostability of the I-OnuI HE variant compared to the parent I-OnuI HE.

In some embodiments, an I-OnuI homing endonuclease (HE) variant that cleaves a target site in the human TCRα gene, comprises one or more amino acid substitutions relative to a parent I-OnuI HE sequence, wherein the one or more amino acid substitutions increase the thermostability of the I-OnuI HE variant compared to the parent I-OnuI HE.

In further embodiments, an I-OnuI homing endonuclease (HE) variant that cleaves a target site in the human CBLB gene, comprises one or more amino acid substitutions relative to a parent I-OnuI HE sequence, wherein the one or more amino acid substitutions increase the thermostability of the I-OnuI HE variant compared to the parent I-OnuI HE.

In particular embodiments, an I-OnuI homing endonuclease (HE) variant that cleaves a target site in the human CTLA-4 gene, comprises one or more amino acid substitutions relative to a parent I-OnuI HE sequence, wherein the one or more amino acid substitutions increase the thermostability of the I-OnuI HE variant compared to the parent I-OnuI HE.

In certain embodiments, an I-OnuI homing endonuclease (HE) variant that cleaves a target site in the human TGFβRII gene, comprises one or more amino acid substitutions relative to a parent I-OnuI HE sequence, wherein the one or more amino acid substitutions increase the thermostability of the I-OnuI HE variant compared to the parent I-OnuI HE.

In additional embodiments, I-OnuI homing endonuclease (HE) variant that cleaves a target site in the human TIM3 gene, comprises one or more amino acid substitutions relative to a parent I-OnuI HE sequence, wherein the one or more amino acid substitutions increase the thermostability of the I-OnuI HE variant compared to the parent I-OnuI HE.

In particular embodiments, an I-OnuI HE variant comprises three or more amino acid substitutions is at an amino acid position selected from the group consisting of: I14, A19, K108, V116, K156, F168, S176, D208, E231, N246, V261, L263, E277, and G300.

In particular embodiments, an I-OnuI HE variant comprises the amino acid substitutions at the following amino acid positions: 114, A19, F168, D208, and N246.

In certain embodiments, an I-OnuI HE variant comprises three or more amino acid substitutions is at an amino acid position selected from the group consisting of: I14, A19, K108, V116, K156, F168, S176, D208, E231, N246, V261, L263, E277, and G300; and one or more amino acid substitutions is at an amino acid position selected from the group consisting of: N31, N33, K52, Y97, K124, K147, I153, K209, E264, and D268.

In particular embodiments, an I-OnuI HE variant comprises five or more amino acid substitutions is at an amino acid position selected from the group consisting of: I14, A19, K108, V116, K156, F168, S176, D208, E231, N246, V261, L263, E277, and G300.

In further embodiments, an I-OnuI HE variant comprises five or more amino acid substitutions is at an amino acid position selected from the group consisting of: 114, A19, K108, V116, K156, F168, S176, D208, E231, N246, V261, L263, E277, and G300; and one or more amino acid substitutions is at an amino acid position selected from the group consisting of: N31, N33, K52, Y97, K124, K147, I153, K209, E264, and D268.

In particular embodiments, an I-OnuI HE variant has a $TM_{50}$ at least 10° C. higher than the $TM_{50}$ of the parent I-OnuI HE.

In some embodiments, an I-OnuI HE variant has a $TM_{50}$ at least 15° C. higher than the $TM_{50}$ of the parent I-OnuI HE.

In certain embodiments, an I-OnuI HE variant has a $TM_{50}$ at least 20° C. higher than the $TM_{50}$ of the parent I-OnuI HE.

In particular embodiments, an I-OnuI HE variant has a $TM_{50}$ at least 25° C. higher than the $TM_{50}$ of the parent I-OnuI HE.

BRIEF DESCRIPTION OF THE SEQUENCE IDENTIFIERS

Figure 1:
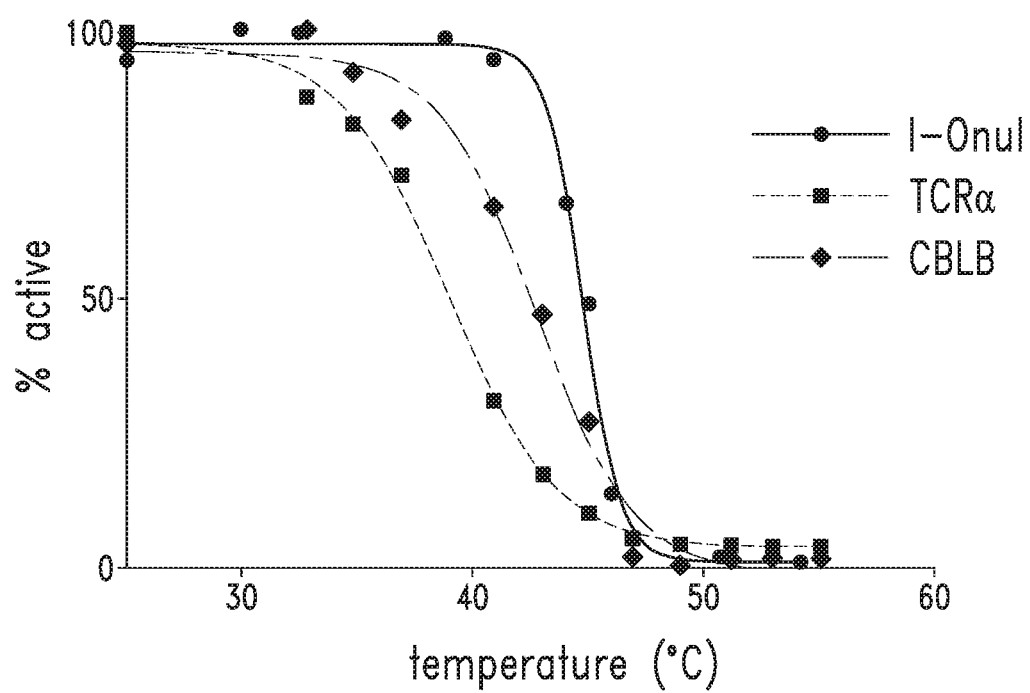
FIG. 1 shows the melt curves for I-OnuI LHE, and I-OnuI LHE variants reprogrammed to target CBLB and TCRα using a yeast surface display-based assay.

SEQ ID NO: 1 is an amino acid sequence of a wild type I-OnuI LAGLIDADG homing endonuclease (LHE).

SEQ ID NO: 2 is an amino acid sequence of a wild type I-OnuI LHE.

SEQ ID NO: 3 is an amino acid sequence of a biologically active fragment of a wild-type I-OnuI LHE.

SEQ ID NO: 4 is an amino acid sequence of a biologically active fragment of a wild-type I-OnuI LHE.

SEQ ID NO: 5 is an amino acid sequence of a biologically active fragment of a wild-type I-OnuI LHE.

SEQ ID NO: 6 is an amino acid sequence of an I-OnuI LHE variant reprogrammed to bind and cleave a target site in the human TCRα gene.

SEQ ID NO: 7 is an amino acid sequence of an I-OnuI LHE variant reprogrammed to bind and cleave a target site in the human CBLB gene.

SEQ ID NO: 8 is an amino acid sequence of an I-OnuI LHE variant reprogrammed to bind and cleave a target site in the human BCL11A gene.

SEQ ID NOs: 9-14 set forth the amino acid sequences of I-OnuI LHE thermostable variants reprogrammed to bind and cleave a target site in the human BCL11A gene.

SEQ ID NO: 15 is an amino acid sequence of an I-OnuI LHE variant reprogrammed to bind and cleave a target site in the human PDCD-1 gene.

SEQ ID NO: 16 is an amino acid sequence of an I-OnuI LHE thermostable variant reprogrammed to bind and cleave a target site in the human PDCD-1 gene.

SEQ ID NO: 17 is an amino acid sequence of an I-OnuI LHE thermostable variant reprogrammed to bind and cleave a target site in the human TCRα gene.

SEQ ID NO: 18 is an amino acid sequence of an I-OnuI LHE thermostable variant reprogrammed to bind and cleave a target site in the human CBLB gene.

SEQ ID NO: 19 is an mRNA encoding a BCL11A I-OnuI HE variant.

SEQ ID NO: 20 is a codon optimized mRNA encoding a BCL11A I-OnuI HE variant.

SEQ ID NO: 21 is an mRNA encoding a BCL11A I-OnuI HE thermostable variant.

SEQ ID NO: 22 is an amino acid sequence that encodes a PDCD-1 megaTAL.

SEQ ID NO: 23 is an amino acid sequence that encodes a PDCD-1 megaTAL thermostable variant.

SEQ ID NOs: 24-34 set forth the amino acid sequences of various linkers.

SEQ ID NOs: 35-59 set forth the amino acid sequences of protease cleavage sites and self-cleaving polypeptide cleavage sites.

In the foregoing sequences, X, if present, refers to any amino acid or the absence of an amino acid.

DETAILED DESCRIPTION

A. Overview

The present disclosure generally relates to, in part, improved genome editing compositions and methods of use thereof. Genome editing enzymes hold tremendous promise for treating diseases, disorders, and conditions with a genetic component. To date, genome editing enzymes engineered to bind and cleave target sites in the genome may have short half-lives in vivo and/or fail to cleave with high efficiency. Without wishing to be bound to any particular theory, the inventors have discovered that homing endonuclease scaffolds can be engineered to increase thermostability and catalytic activity and that homing endonuclease activity unexpectedly increased when the enzymes were engineered to have greater thermostability. Moreover, the amino acid positions of homing endonucleases altered to increase thermostability and activity and reprogrammed to bind and cleave one target site are conserved and can be used to increase thermostability of other homing endonucleases reprogrammed to bind and cleave other target sites.

Genome editing compositions and methods contemplated in various embodiments comprise nuclease variants with enhanced stability and activity, designed to bind and cleave a target sequence present in a genome. The nuclease variants contemplated in particular embodiments, can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

In particular embodiments, homing endonucleases comprise one or more amino acid substitutions that increase stability and/or activity. In particular embodiments, homing endonucleases comprise 1, 2, 3, 4, 5, 6, 7, 8, 9, 10 or more amino acid substitutions that increase stability and/or activity.

In particular embodiments, homing endonucleases comprise one or more amino acid substitutions that increase stability and/or activity are formatted as a megaTAL. In particular embodiments, a megaTAL comprises a homing endonuclease that has 1, 2, 3, 4, 5, 6, 7, 8, 9, 10 or more amino acid substitutions that increase stability and/or activity.

In certain embodiments, compositions contemplated herein comprise a homing endonuclease variant or megaTAL that has been modified to increase stability and/or activity and optionally, an end-processing enzyme, e.g., Trex2.

In various embodiments, a cell or population of cells comprises a homing endonuclease variant or megaTAL that has been modified to increase stability and/or activity.

Accordingly, the methods and compositions contemplated herein represent a quantum improvement compared to existing adoptive cell therapies.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir andCC Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length=15%, +10%, +9%, +8%, +7%, +6%, +5%, +4%, +3%, +2%, or +1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a nuclease variant to produce, elicit, or cause a greater response (i.e., physiological response) compared to the response caused by either vehicle or control. A measurable response may include an increase in stability, e.g., thermostability, catalytic activity and/or binding affinity of a homing endonuclease variant relative to a parent homing endonuclease from which the variant was derived. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By "decrease" or "lower" or "lessen" or "reduce" or "abate" or "ablate" or "inhibit" or "dampen" refers generally to the ability of a nuclease variant contemplated herein to produce, elicit, or cause a lesser response (i.e., physiological response) compared to the response caused by either vehicle or control. A measurable response may include a decrease in lability, off-target binding affinity, off-target cleavage specificity, of a homing endonuclease variant relative to a parent homing endonuclease from which the variant was derived. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By "maintain," or "preserve," or "maintenance," or "no change," or "no substantial change," or "no substantial decrease" refers generally to the ability of a nuclease variant to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement. In a preferred embodiment, the target site is a sequence in a human PDCD-1 gene.

"Protein stability" refers to the net balance of forces, which determine whether a protein will be its native folded conformation or a denatured (unfolded or extended) state. Protein unfolding, either partial or complete, can result in loss of function along with degradation by the cellular machinery. Polypeptide stability can be measured in response to various conditions including but not limited to temperature, pressure, and osmolyte concentration.

"Thermostability" refers to the ability of a protein to properly fold or remain in its native folded conformation and resist denaturation or unfolding upon exposure to temperature fluctuations. At non-ideal temperatures a protein will either not be able to efficiently fold into an active confirmation or will have the propensity to unfold from its active confirmation. A protein with increased thermostability will fold properly and retain activity over an increased range of temperatures when compared to a protein that is less thermostable.

"$TM_{50}$" refers to the temperature at which 50% of an amount of protein is unfolded. In particular embodiments, the TMso is the temperature at which an amount of protein has 50% maximum activity. In particular embodiments, $TM_{50}$ is a specific value determined by fitting multiple data points to a Boltzmann sigmoidal curve. In one non-limiting example, the $TM_{50}$ of a protein is measured in a yeast surface display activity assay by expressing the protein on the yeast surface at ~25° C., aliquoting the yeast into multiple wells and exposing to a range of higher temperatures, cooling the yeast, and then measuring cleavage activity of the enzyme. As the temperature increases, more of the proteins lose their active confirmation, and therefore fewer protein expressing cells display sufficient activity to measure cleavage with flow cytometry. The temperature at which 50% of yeast display population is active as compared to the non-heat shocked population is the $TM_{50}$.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part of or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may increase the likelihood of imprecise repair.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression and/or function of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

C. Nuclease Variants

Various engineered nucleases may lack sufficient stability to be used in a clinical setting. Nuclease variants contemplated herein have been modified to increase thermostability and enzymatic activity to enable clinical use of previously unstable enzymes. The nuclease variants are suitable for genome editing a target site and comprise one or more DNA binding domains and one or more DNA cleavage domains (e.g., one or more endonuclease and/or exonuclease domains), and optionally, one or more linkers contemplated herein. The engineered nucleases comprise one or amino acid substitutions that increase thermostability and/or activity compared to a reference or parent nuclease. The terms "reprogrammed nuclease," "engineered nuclease," or "nuclease variant" are used interchangeably and refer to a nuclease comprising one or more DNA binding domains and one or more DNA cleavage domains, wherein the nuclease has been designed to bind and cleave a double-stranded DNA target sequence and modified to increase thermostability and/or activity of the nuclease.

A "reference nuclease" or "parent nuclease" refers to a wild type nuclease, a nuclease found in nature, or a nuclease or variant that is modified to increase basal activity, affinity, specificity, selectivity, and/or stability to generate a subsequent nuclease variant.

In particular embodiments, a nuclease variant binds comprises at least 1 amino acid substitution that increases the stability and/or activity of the variant relative to a parent nuclease. In particular embodiments, a nuclease variant binds comprises at least 1, at least 2, at least 3, at least 4, at least 5, at least 6, at least 7, at least 8, at least 9, or at least 10 amino acid substitution that increases the stability and/or activity of the variant relative to a parent nuclease.

Nuclease variants may be designed and/or modified from a naturally occurring nuclease or from an existing nuclease variant. In preferred embodiments, a nuclease variant comprises increased thermostability and/or enzymatic activity compared to a parent nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerases or template-independent DNA polymerase activity.

Illustrative examples of nuclease variants reprogrammed to bind and cleave a target sequence and engineered to have increased thermostability include, but are not limited to, homing endonuclease (meganuclease) variants and megaTALs. In particular embodiments, the nuclease variants are reprogrammed to bind a target site or sequence in a gene selected from the group consisting of: HBA, HBB, HBG1, HBG2, BCL11A, PCSK9, TCRA, TCRB, B2M, HLA-A, HLA-B, HLA-C, HLA-E, HLA-F, HLA-G, CIITA, AHR, PD-1, CTLA4, TIGIT, TGFβR2, LAG-3, TIM-3, BTLA, ILAR, IL6R, CXCR1, CXCR2, IL10R, IL13Rα2, TRAILR1, RCAS1R, and FAS.

1. Homing Endonuclease (Meganuclease) Variants

Homing endonucleases (meganucleases) are genome editing enzymes that can reprogrammed to bind and cleave selected target sites. However, some reprogrammed homing endonucleases were not sufficiently stable to allow further development or clinical use. The present inventors have unexpectedly discovered that certain amino acid positions in homing endonucleases affect stability, e.g., thermostability, of the enzymes; and further, substitution of amino acids at these positions can enhance enzyme stability compared to the parent enzyme, without sacrificing affinity or activity of the enzyme.

In various embodiments, a homing endonuclease or meganuclease is reprogrammed to introduce a double-strand break (DSB) in a target site and engineered to increase its thermostability, affinity, specificity, selectivity, and/or enzymatic activity. In preferred embodiments, a homing endonuclease is reprogrammed to bind and cleave a target site and engineered to increase the enzyme's thermostability relative to the thermostability of the enzyme from which it was designed.

"Homing endonuclease" and "meganuclease" are used interchangeably and refer to naturally-occurring homing endonucleases that recognize 12-45 base-pair cleavage sites and are commonly grouped into five families based on sequence and structure motifs: LAGLIDADG, GIY-YIG, HNH, His-Cys box, and PD-(D/E) XK.

A "reference homing endonuclease," "reference meganuclease," "parent homing endonuclease," or "parent meganuclease" refers to a wild type homing endonuclease, a homing endonuclease found in nature, or a homing endonuclease that has been modified to increase basal activity, affinity, and/or stability to generate a subsequent homing endonuclease variant.

An "engineered homing endonuclease," "reprogrammed homing endonuclease," "homing endonuclease variant," "engineered meganuclease," "reprogrammed meganuclease," or "meganuclease variant" refers to a homing endonuclease comprising one or more DNA binding domains and one or more DNA cleavage domains, wherein the homing endonuclease has been designed and/or modified from a parental or naturally occurring homing endonuclease to bind and cleave a DNA target sequence; has optionally undergone one or more rounds of refining affinity, selectivity, specificity, and/or activity; and has further been modified to have increased thermostability. Homing endonuclease variants may be designed and/or modified from a naturally occurring homing endonuclease or from another homing endonuclease variant. Homing endonuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template dependent DNA polymerase or template-independent DNA polymerase activity.

Homing endonuclease variants do not exist in nature and can be obtained by recombinant DNA technology or by random mutagenesis. Homing endonuclease variants may be obtained by making one or more amino acid alterations, e.g., mutating, substituting, adding, or deleting one or more amino acids, in a naturally occurring homing endonuclease or homing endonuclease variant. In particular embodiments, a homing endonuclease variant comprises one or more amino acid alterations to the DNA recognition interface to bind and cleave a selected target sequence and one or more amino acid substitutions to increase thermostability.

Homing endonuclease variants contemplated in particular embodiments may further comprise one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. In particular embodiments, homing endonuclease variants are introduced into a cell with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. The homing endonuclease variant and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the homing endonuclease amino acid residues that interact with nucleic acid target bases as well as those residues that are adjacent. For each homing endonuclease, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or homing endonuclease variant. By way of non-limiting example, a homing endonuclease variant contemplated in particular embodiments may be derived by constructing libraries of HE variants in which one or more amino acid residues localized in the DNA recognition interface of the natural homing endonuclease (or a previously generated homing endonuclease variant) are varied. The libraries may be screened for target cleavage activity against each target site using cleavage assays (see e.g., Jarjour et al., 2009. Nuc. Acids Res. 37 (20): 6871-6880).

LAGLIDADG homing endonucleases (LHE) are the most well studied family of homing endonucleases, are primarily encoded in archaea and in organellar DNA in green algae and fungi, and display the highest overall DNA recognition specificity.

In one embodiment, a reprogrammed LHE or LHE variant that has been engineered to enhance thermostability is an I-OnuI HE variant (I-OnuI LHE variant). See e.g., SEQ ID NOs: 8-14 and 16-18.

In one embodiment, a reprogrammed I-OnuI HE or I-OnuI HE variant engineered to increase thermostability is generated from a natural I-OnuI, I-OnuI HE variant, or biologically active fragment thereof (e.g., SEQ ID NOs: 1-8 and 15). In preferred embodiments, a reprogrammed I-OnuI HE or I-OnuI HE variant engineered to increase thermostability is generated from an existing I-OnuI HE variant. In even more preferred embodiments, a reprogrammed I-OnuI HE or I-OnuI HE variant engineered to increase thermostability comprises 1, 2, 3, 4, 5, 6, 7, 8, 9, or 10 or more amino acid substitutions to increase thermostability of the enzyme compared to the thermostability of an existing parent I-OnuI HE variant.

In certain embodiments, an I-OnuI HE variant comprises at least 1, at least 2, at least 3, at least 4, at least 5, at least 6, or 7 amino acid substitutions of the following amino acid positions that have been identified to individually and collectively increase homing endonuclease thermostability: I14, A19, V116, F168, D208, N246, and L263 of representative I-OnuI amino acid sequences (SEQ ID NOs: 1-8 and 15), biologically active fragments thereof, and/or further variants thereof.

I In certain embodiments, an I-OnuI HE variant comprises amino acid substitutions of the following amino acid positions that have been identified to individually and collectively increase homing endonuclease thermostability: 114, A19, F168, D208, and N246 of representative I-OnuI amino acid sequences (SEQ ID NOs: 1-8 and 15), biologically active fragments thereof, and/or further variants thereof.

n particular embodiments, the amino acid substitution for I14 is selected from the group consisting of: I14S, I14N, I14M, I14K, I14F, I14D, I14T, and I14V. In preferred embodiments, the amino acid substitution for I14 is I14T or I14V. In particular embodiments, the amino acid substitution for A19 is selected from the group consisting of: A19C, A19D, A19I, A19L, A19S, A19T, and A19V. In preferred embodiments, the amino acid substitution for A19 is A19T or A19V. In particular embodiments, the amino acid substitution for V116 is selected from the group consisting of: V116F, V116D, V116A, V116L, and V116I. In preferred embodiments, the amino acid substitution for V116 is V116L or V116I. In particular embodiments, the amino acid substitution for F168 is selected from the group consisting of: F168H, F168Y, F168I, F168V, F168P, F168L, and F168S. In preferred embodiments, the amino acid substitution for F168 is F168L and F168S. In particular embodiments, the amino acid substitution for D208 is selected from the group consisting of: D208N, D208Y, D208V, and D208E. In preferred embodiments, the amino acid substitution for D208 is D208E. In preferred embodiments, the amino acid substitution for F168 is F168L, and F168S. In particular embodiments, the amino acid substitution for N246 is selected from the group consisting of: N246H, N246I, N246D, N246R, N246S, N246T, N246V, N246Y, and N246K. In preferred embodiments, the amino acid substitution for N246 is N246K. In particular embodiments, the amino acid substitution for L263 is selected from the group consisting of: L263H, L263F, L263P, L263T, L263V, and L263R. In preferred embodiments, the amino acid substitution for L263 is L263R.

In certain embodiments, an I-OnuI HE variant comprises at least 1, at least 2, at least 3, at least 4, at least 5, at least 6, or 7 amino acid substitutions of the following amino acid positions that have been identified to individually and collectively increase homing endonuclease thermostability: K108, K156, S176, E231, V261, E277, and G300 of representative I-OnuI amino acid sequences (SEQ ID NOs: 1-8 and 15), biologically active fragments thereof, and/or further variants thereof.

In particular embodiments, the amino acid substitution for K108 is selected from the group consisting of: K108E, K108N, K108Q, K108R, K108T, K108V, and K108M. In preferred embodiments, the amino acid substitution for K108 is K108M. In particular embodiments, the amino acid substitution for K156 is selected from the group consisting of: K156N, K156Q, K156R, K156T, K156V, K156I and K156E. In preferred embodiments, the amino acid substitution for K156 is K156I or K156E. In particular embodiments, the amino acid substitution for S176 is S176P, S176N or S176A. In preferred embodiments, the amino acid substitution for S176 is S176A. In particular embodiments, the amino acid substitution for E231 is selected from the group consisting of: E231D, E231V, E231K, and E231G. In preferred embodiments, the amino acid substitution for E231 is E231K or E231G. In particular embodiments, the amino acid substitution for V261 is selected from the group consisting of: V261D, V261G, V261I, V261L, V261S, V261T and V261A. In preferred embodiments, the amino acid substitution for V261 is V261A. In particular embodiments, the amino acid substitution for E277 is selected from the group consisting of: E277A, E277D, E277G, E277Q, E277V, and E277K. In preferred embodiments, the amino acid substitution for E277 is E277K. In particular embodiments, the amino acid substitution for G300 is selected from the group consisting of: G300S, G300V, G300D, G300C, and G300R. In preferred embodiments, the amino acid substitution for G300 is G300R.

Without wishing to be bound by any particular theory, the inventors have also discovered that each homing endonuclease reprogrammed to bind and cleave a particular target sequence may one or more additional amino acid positions that affect thermostability. In certain embodiments, an I-OnuI HE variant comprises at least 1, at least 2, at least 3, at least 4, at least 5, at least 6, at least 7, at least 8, at least 9, or 10 amino acid substitutions of the following amino acid positions that have been identified to individually, and in some cases collectively, increase homing endonuclease thermostability: N31, N33, K52, Y97, K124, K147, I153, K209, E264, and D268 of representative I-OnuI amino acid sequences (SEQ ID NOs: 1-8 and 15), biologically active fragments thereof, and/or further variants thereof.

In particular embodiments, the amino acid substitution for N31 is selected from the group consisting of: N31D, N31H, N31I, N31R, N31K, N31S, N31T and N31Y. In particular embodiments, the amino acid substitution for N31 is N31K. In particular embodiments, the amino acid substitution for N33 is selected from the group consisting of: N33D, N33G, N33H, N33I, N33K, N33S, N33T and N33Y. In particular embodiments, the amino acid substitution for N33 is N33K. In particular embodiments, the amino acid substitution for K52 is selected from the group consisting of: K52Q, K52R, K52T, K52Y, K52N, K52E, and K52M. In preferred embodiments, the amino acid substitution for K52 is K52M. In particular embodiments, the amino acid substitution for Y97 is selected from the group consisting of: Y97H, Y97N, and Y97F. In particular embodiments, the amino acid substitution for Y97 is Y97F. In particular embodiments, the amino acid substitution for K124 is selected from the group consisting of: K124E, K124N, K124R and K124T. In particular embodiments, the amino acid substitution for K124 is K124N. In particular embodiments, the amino acid substitution for K147 is selected from the group consisting of: K147E, K147I, K147N, K147R and K147T. In particular embodiments, the amino acid substitution for K147 is K147I. In particular embodiments, the amino acid substitution for I153 is selected from the group consisting of: I153D, I153H, I153K, I153T, I153Y, I153S, I153V and I153N. In preferred embodiments, the amino acid substitution for I153 is I153N. In particular embodiments, the amino acid substitution for K209 is selected from the group consisting of: K209E, K209M, K209N, K209Q and K209R. In particular embodiments, the amino acid substitution for K209 is K209R. In particular embodiments, the amino acid substitution for E264 is selected from the group consisting of: E264A, E264D, E264G, E264K, E264Q, E264R and E264V. In particular embodiments, the amino acid substitution for E264 is E264K. In particular embodiments, the amino acid substitution for D268 is selected from the group consisting of: D268A, D268E, D268G, D268H, D268N, D268V and D268Y. In particular embodiments, the amino acid substitution for D268 is D268N.

In particular embodiments, an I-OnuI HE variant comprises one or more, two or more, three or more, four or more, five or more, six or more, seven or more, eight or more, nine or more, 10 or more, 11 or more, 12 or more, 13 or more, or 14 amino acid substitutions of the following amino acid positions that have been identified to individually and collectively increase homing endonuclease thermostability: I14, A19, K108, V116, K156, F168, S176, D208, E231, N246, V261, L263, E277, and G300 of representative I-OnuI amino acid sequences (SEQ ID NOs: 1-8 and 15), biologically active fragments thereof, and/or further variants thereof.

In particular embodiments, an I-OnuI HE variant comprises one or more, two or more, three or more, four or more, five or more, six or more, seven or more, eight or more, nine or more, 10 or more, 11 or more, 12 or more, 13 or more, or 14 amino acid substitutions of the following amino acid positions that have been identified to individually and collectively increase homing endonuclease thermostability: I14, A19, K108, V116, K156, F168, S176, D208, E231, N246, V261, L263, E277, and G300; and one or more, two or more, three or more, four or more, five or more, six or more, seven or more, eight or more, nine or more, or 10 amino acid substitutions of the following amino acid positions that have been identified to individually, and in some cases collectively, increase homing endonuclease thermostability: N31, N33, K52, Y97, K124, K147, I153, K209, E264, and D268; of representative I-OnuI amino acid sequences (SEQ ID NOs: 1-8 and 15), biologically active fragments thereof, and/or further variants thereof.

In particular embodiments, an I-OnuI HE variant that binds and cleaves a target sequence comprises one or more, two or more, three or more, four or more, five or more, six or more, seven or more, eight or more, nine or more, or 10 amino acid substitutions to increase thermostability and is at least 85%, at least 86%, at least 87%, at least 88%, at least 89%, at least 90%, at least 91%, at least 92%, at least 93%, at least 94%, at least 95%, at least 96%, at least 97%, or at least 98% or at least 99% identical to the amino acid sequence set forth in any one of SEQ ID NOs: 1-18 or a biologically active fragment thereof.

In particular embodiments, an I-OnuI HE variant has increased thermostability compared to a parent I-OnuI LHE variant. In particular embodiments, an I-OnuI HE variant has a $TM_{50}$ about 5° C. higher to about 35° C. higher, about 10° C. higher to about 35° C. higher, about 10° C. higher to about 30° C. higher, about 10° C. higher to about 25° C. higher about 15° C. higher to about 35° C. higher about 15° C. higher to about 30° C., or about 15° C. higher to about 25° C. higher than the TMso of a parent I-OnuI HE or reference I-OnuI HE.

In particular embodiments, an I-OnuI HE variant has increased thermostability compared to a parent or reference I-OnuI LHE variant. In particular embodiments, an I-OnuI HE variant has a $TM_{50}$ about 5° C. higher, about 6° C. higher, about 7° C. higher, about 8° C. higher, about 9° C. higher, about 10° C. higher, about 11° C. higher, about 12° C. higher, about 13° C. higher, about 14° C. higher, about 15° C., about 16° C. higher, about 17° C. higher, about 18° C. higher, about 19° C. higher, about 20° C. higher, about 21° C. higher, about 22° C. higher, about 23° C. higher, about 24° C. higher, about 25° C. higher, about 26° C. higher, about 27° C. higher, about 28° C. higher, about 29° C. higher, about 30° C. higher, about 31° C. higher, about 32° C. higher, about 33° C. higher, about 34° C. higher, or about 35° C. higher than the $TM_{50}$ of a parent I-OnuI HE or reference I-OnuI HE.

In particular embodiments, an I-OnuI HE variant comprising one or more mutations to enhance thermostability is reprogrammed to bind a target site or sequence in a gene selected from the group consisting of: HBA, HBB, HBG1, HBG2, BCL11A, PCSK9, TCRA, TCRB, B2M, HLA-A, HLA-B, HLA-C, HLA-E, HLA-F, HLA-G, CIITA, AHR, PD-1, CTLA4, TIGIT, TGFβR2, LAG-3, TIM-3, BTLA, IL4R, IL6R, CXCR1, CXCR2, IL10R, IL13Rα2, TRAILR1, RCAS1R, and FAS.

2. MegaTALS

MegaTALs are genome editing enzymes that combine the DNA binding properties of TAL DNA binding domains with the DNA binding and cleavage activities of homing endonucleases. Without wishing to be bound by any particular theory, it is believed that when a relatively unstable homing endonuclease is formatted as a megaTAL, the megaTAL is not inherently stabilized. Accordingly, introducing one or more stabilizing mutations into a homing endonuclease similarly stabilizes the corresponding megaTAL.

In various embodiments, a megaTAL comprises one or more TAL DNA binding domains and a homing endonuclease or meganuclease reprogrammed to introduce a double-strand break (DSB) in a target site and engineered to increase its thermostability, affinity, specificity, selectivity, and/or enzymatic activity of the enzyme. In preferred embodiments, the increased thermostability of a megaTAL comprising a homing endonuclease engineered to increase the enzyme's thermostability is relative to the thermostability of a megaTAL comprising the homing endonuclease before engineering to increase its thermostability.

A "megaTAL" refers to a polypeptide comprising a TALE DNA binding domain and a homing endonuclease variant that binds and cleaves a DNA target sequence and that has been engineered for increased thermostability, and optionally comprises one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase or template-independent DNA polymerase activity.

A "reference megaTAL" or "parent megaTAL" refers to a megaTAL that comprises a TALE DNA binding domain and a wild type homing endonuclease, a homing endonuclease found in nature, or a homing endonuclease that is modified to increase basal activity, affinity, and/or stability to generate a subsequent homing endonuclease variant.

In particular embodiments, a megaTAL can be introduced into a cell along with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase, or template-independent DNA polymerase activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs, e.g., AvrBs3 from *Xanthomonas campestris* pv. *vesicatoria, Xanthomonas gardneri, Xanthomonas translucens, Xanthomonas axonopodis, Xanthomonas perforans, Xanthomonas alfalfa, Xanthomonas citri, Xanthomonas euvesicatoria,* and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S*for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-15 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-15.5 repeat units, more preferably 7.5-15.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises a TAL effector architecture comprising an "N-terminal domain (NTD)" polypeptide, one or more TALE repeat domains/units, a "C-terminal domain (CTD)" polypeptide, and a homing endonuclease variant. In some embodiments, the NTD, TALE repeats, and/or CTD domains are from the same species. In other embodiments, one or more of the NTD, TALE repeats, and/or CTD domains are from different species.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids+1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids+1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a homing endonuclease reprogrammed to bind and cleave a target sequence and engineered to increase enzyme stability and/or activity, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to a homing endonuclease variant. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the homing endonuclease variant. In this way, the megaTALs contemplated herein, increase the specificity and efficiency of genome editing.

In one embodiment, a megaTAL comprises a homing endonuclease variant and a TALE DNA binding domain that binds a nucleotide sequence that is within about 2, 3, 4, 5, or 6 nucleotides upstream of the binding site of the reprogrammed homing endonuclease.

In particular embodiments, a megaTAL contemplated herein, comprises one or more TALE DNA binding repeat units and an I-OnuI HE variant comprising increased thermostability and/or enzymatic activity compared to a parent I-OnuI HE variant.

In particular embodiments, a megaTAL contemplated herein, comprises an NTD, one or more TALE DNA binding repeat units, a CTD, and an I-OnuI HE variant comprising increased thermostability and/or enzymatic activity compared to a parent I-OnuI HE variant.

In particular embodiments, a megaTAL contemplated herein, comprises an NTD, about 9.5 to about 15.5 TALE DNA binding repeat units, and an I-OnuI HE variant comprising increased thermostability and/or enzymatic activity compared to a parent I-OnuI HE variant.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an I-OnuI HE variant comprising increased thermostability and/or enzymatic activity compared to a parent I-OnuI HE variant. In particular embodiments, any one of, two of, or all of the NTD, DNA binding domain, and CTD can be designed from the same species or different species, in any suitable combination.

In particular embodiments, a megaTAL comprising an I-OnuI HE variant that has one or more mutations to enhance thermostability is reprogrammed to bind a target site or sequence in a gene selected from the group consisting of: HBA, HBB, HBG1, HBG2, BCL11A, PCSK9, TCRA, TCRB, B2M, HLA-A, HLA-B, HLA-C, HLA-E, HLA-F, HLA-G, CIITA, AHR, PD-1, CTLA4, TIGIT, TGFβR2, LAG-3, TIM-3, BTLA, ILAR, IL6R, CXCR1, CXCR2, IL10R, IL13Rα2, TRAILR1, RCAS1R, and FAS.

3. End-Processing Enzymes

Genome editing compositions and methods contemplated in particular embodiments comprise editing cellular genomes using an I-OnuI HE variant comprising increased thermostability and/or enzymatic activity compared to a parent I-OnuI HE variant and one or more copies of an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme. In particular embodiments, genome editing compositions comprise a polynucleotide encoding a homing endonuclease variant end-processing enzyme single polypeptide fusion in addition to a tandem copy of the end-processing enzyme separated by a self-cleaving peptide.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using and an I-OnuI HE variant comprising increased thermostability and/or enzymatic activity compared to a parent I-OnuI HE variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, Mre11, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), Apel, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising an I-OnuI HE variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, *E. coli* ExoI, hTREX2, mouse TREX2, rat TREX2, hTREX1, mouse TREX1, rat TREX1, and Rat TREX1.

In particular embodiments, the DNA end-processing enzyme is a 3' to 5' exonuclease, preferably Trex 1 or Trex2, more preferably Trex2, and even more preferably human or mouse Trex2.

D. Polypeptides

Various polypeptides are contemplated herein, including, but not limited to, homing endonuclease variants and megaTALs engineered to increase thermostability and/or enzymatic activity, and fusion polypeptides. In preferred embodiments, a polypeptide comprises the amino acid sequence set forth in any one or SEQ ID NOs: 9-14, 16-18, 22, and 23. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances. In particular embodiments, an isolated polypeptide is a synthetic polypeptide, a semi-synthetic polypeptide, or a polypeptide obtained or derived from a recombinant source.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a homing endonuclease, megaTAL or the like that binds and cleaves a target site by introducing one or more substitutions, deletions, additions and/or insertions into the polypeptide that increase thermal stability. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to a reference sequence, typically where the variant maintains at least one biological activity of the reference sequence.

In preferred embodiments, polypeptide variants include homing endonucleases or megaTALs that have been engineered to increase their thermostability and/or activity. I-OnuI HE polypeptides or fragments thereof can be reprogrammed to bind and cleave a target site. In particular embodiments, a reprogrammed I-OnuI HE variant has relatively low thermostability and/or activity compared to a parent I-OnuI HE. In preferred embodiments, an I-OnuI homing endonuclease or fragment thereof is engineered to bind and cleave a target site and to increase thermostability and/or activity of the enzyme.

Polypeptide variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, a polypeptide comprises a biologically active fragment of a homing endonuclease variant or a megaTAL. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

A biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a homing endonuclease variant compared to a corresponding wild type homing endonuclease sequence, more preferably a deletion of the 4 N-terminal amino acids of a homing endonuclease variant compared to a corresponding wild type homing endonuclease sequence. In a particular embodiment, a biologically active fragment lacks or comprises a deletion of the 1, 2, 3, 4, or 5 C-terminal amino acids of a homing endonuclease variant compared to a corresponding wild type homing endonuclease sequence, more preferably a deletion of the 2 C-terminal amino acids of a homing endonuclease variant compared to a corresponding wild type homing endonuclease sequence. In a particular preferred embodiment, a biologically active fragment lacks or comprises a deletion of the 4 N-terminal amino acids and 2 C-terminal amino acids of a homing endonuclease variant compared to a corresponding wild type homing endonuclease sequence.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1, 2, 3, 4, or 5 C-terminal amino acids: R, G, S, F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1, 2, 3, 4, or 5 C-terminal amino acids: R, G, S, F, V.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1 or 2 C-terminal amino acids: F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1 or 2 C-terminal amino acids: F, V.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82:488-492), Kunkel et al., (1987, *Methods in Enzymol,* 154:367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (*Natl. Biomed. Res. Found.*, Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | | GCU | |
| Cysteine | C | Cys | UGC | | | | UGU | |
| Aspartic acid | D | Asp | GAC | | | | GAU | |
| Glutamic acid | E | Glu | GAA | | | | GAG | |
| Phenylalanine | F | Phe | UUC | | | | UUU | |
| Glycine | G | Gly | GGA | GGC | GGG | | GGU | |
| Histidine | H | His | CAC | | | | CAU | |
| Isoleucine | I | Iso | AUA | AUC | | | AUU | |
| Lysine | K | Lys | AAA | | | | AAG | |
| Leucine | L | Leu | UUA | UUG | CUA | CUC | CUG | CUU |
| Methionine | M | Met | | | AUG | | | |
| Asparagine | N | Asn | AAC | | | | AAU | |
| Proline | P | Pro | CCA | CCC | CCG | | CCU | |
| Glutamine | Q | Gln | CAA | | | | CAG | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU | |
| Valine | V | Val | GUA | GUC | GUG | | GUU | |
| Tryptophan | W | Trp | | | UGG | | | |
| Tyrosine | Y | Tyr | UAC | | | | UAU | |

Guidance in determining which amino acid residues can be substituted, inserted, or deleted in particular embodiments, without abolishing biological activity can be found using computer programs well known in the art, such as DNASTAR, DNA Strider, Geneious, Mac Vector, or Vector NTI software. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, an I-OnuI variant comprises one or more non-conservative amino acid substitutions at positions that affect the thermostability of the enzyme. In one embodiment, an I-OnuI variant comprises one or more conservative and/or non-conservative amino acid substitutions at positions that affect the thermostability of the enzyme.

In particular embodiments, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to, the following amino acid sequences: glycine polymers (G) n; glycine-serine polymers (G1-5S1-5) n, where n is an integer of at least one, two, three, four, or five; glycine-alanine polymers; alanine-serine polymers; GGG (SEQ ID NO: 24); DGGGS (SEQ ID NO: 25); TGEKP (SEQ ID NO: 26) (see e.g., Liu et al., *PNAS* 5525-5530 (1997)); GGRR (SEQ ID NO: 27) (Pomerantz et al. 1995, supra); (GGGGS)$_n$ wherein n=1, 2, 3, 4 or 5 (SEQ ID NO: 28) (Kim et al., *PNAS* 93, 1156-1160 (1996.); EGKSSGSGSESKVD (SEQ ID NO: 29) (Chaudhary et al., 1990, *Proc. Natl. Acad. Sci. U.S.A.* 87:1066-1070); KESGSVSSEQLAQFRSLD (SEQ ID NO: 30) (Bird et al., 1988, *Science* 242:423-426), GGRRGGGS (SEQ ID NO: 31); LRQRDGERP (SEQ ID NO: 32); LRQKDGGGSERP (SEQ ID NO: 33); LRQKD (GGGS)$_2$ERP (SEQ ID NO: 34). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5 (8); 616-26).

Suitable protease cleavages sites and self-cleaving peptides are known to the skilled person (see, e.g., in Ryan et al., 1997. *J. Gener. Virol.* 78, 699-722; Scymczak et al. (2004) *Nature Biotech.* 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ (G/S) (SEQ ID NO: 35), for example, ENLYFQG (SEQ ID NO: 36) and ENLYFQS (SEQ ID NO: 37), wherein X represents any amino acid (cleavage by TEV occurs between Q and G or Q and S).

In particular embodiments, the polypeptide cleavage signal is a viral self-cleaving peptide or ribosomal skipping sequence.

Illustrative examples of ribosomal skipping sequences include but are not limited to: a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of 2A sites are provided in Table 2.

TABLE 2

Exemplary 2A sites include the following sequences:

| | |
|---|---|
| SEQ ID NO: 38 | GSGATNFSLLKQAGDVEENPGP |
| SEQ ID NO: 39 | ATNFSLLKQAGDVEENPGP |
| SEQ ID NO: 40 | LLKQAGDVEENPGP |
| SEQ ID NO: 41 | GSGEGRGSLLTCGDVEENPGP |
| SEQ ID NO: 42 | EGRGSLLTCGDVEENPGP |
| SEQ ID NO: 43 | LLTCGDVEENPGP |
| SEQ ID NO: 44 | GSGQCTNYALLKLAGDVESNPGP |
| SEQ ID NO: 45 | QCTNYALLKLAGDVESNPGP |
| SEQ ID NO: 46 | LLKLAGDVESNPGP |
| SEQ ID NO: 47 | GSGVKQTLNFDLLKLAGDVESNPGP |
| SEQ ID NO: 48 | VKQTLNFDLLKLAGDVESNPGP |
| SEQ ID NO: 49 | LLKLAGDVESNPGP |

TABLE 2 -continued

Exemplary 2A sites include the
following sequences:

| | | |
|---|---|---|
| SEQ ID NO: | 50 | LLNFDLLKLAGDVESNPGP |
| SEQ ID NO: | 51 | TLNFDLLKLAGDVESNPGP |
| SEQ ID NO: | 52 | LLKLAGDVESNPGP |
| SEQ ID NO: | 53 | NFDLLKLAGDVESNPGP |
| SEQ ID NO: | 54 | QLLNFDLLKLAGDVESNPGP |
| SEQ ID NO: | 55 | APVKQTLNFDLLKLAGDVESNPGP |
| SEQ ID NO: | 56 | VTELLYRMKRAETYCPRPLLAIHPTEARHKQKI VAPVKQT |
| SEQ ID NO: | 57 | LNFDLLKLAGDVESNPGP |
| SEQ ID NO: | 58 | LLAIHPTEARHKQKIVAPVKQTLNFDLLKLAGD VESNPGP |
| SEQ ID NO: | 59 | EARHKQKIVAPVKQTLNFDLLKLAGDVESNPGP |

E. Polynucleotides

In particular embodiments, polynucleotides encoding one or more homing endonuclease variants and megaTALs engineered to increase thermostability and/or enzymatic activity, and fusion polypeptides contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include, but are not limited to polynucleotides encoding SEQ ID NOs: 9-14, 16-18, 22, and 23 and polynucleotide sequences set forth in SEQ ID NOs: 19-21.

In various illustrative embodiments, polynucleotides contemplated herein include, but are not limited to polynucleotides encoding homing endonuclease variants, megaTALs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man. In particular embodiments, an isolated polynucleotide is a synthetic polynucleotide, a semi-synthetic polynucleotide, or a polynucleotide obtained or derived from a recombinant source.

In various embodiments, a polynucleotide comprises an mRNA encoding a polypeptide contemplated herein including, but not limited to, a homing endonuclease variant, a megaTAL, and an end-processing enzyme. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, a mRNA encoding a homing endonuclease variant or megaTAL comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5')ppp(5')G, G(5')ppp(5')C, G(5')ppp(5')A; methylated 5' cap analogs, e.g., $m^7$G(5')ppp(5')G, $m^7$G(5')ppp(5')C, and $m^7$G(5')ppp(5')A; dimethylated 5' cap analogs, e.g., $m^{2,7}$G(5')ppp(5')G, $m^{2,7}$G(5')ppp(5')C, and $m^{2,7}$G(5')ppp(5')A; trimethylated 5' cap analogs, e.g., $m^{2,2,7}$G(5')ppp(5')G, $m^{2,2,7}$G(5')ppp(5')C, and $m^{2,2,7}$G(5')ppp(5')A; dimethylated symmetrical 5' cap analogs, e.g., $m^7$G(5')pppm7 (5')G, $m^7$G(5')pppm7 (5')C, and $m^7$G(5')pppm7 (5')A; and anti-reverse 5' cap analogs, e.g., Anti-Reverse Cap Analog (ARCA) cap, designated 3'O-Me-$m^7$G (5')ppp(5')G, 2'O-Me-$m^7$G(5')ppp(5')G, 2'O-Me-$m^7$G(5')ppp(5')C, 2'O-Me-$m^7$G(5')ppp(5')A, $m^7$2'd(5')ppp(5')G, m⁷2'd(5')ppp(5')C, m⁷2'd(5')ppp(5')A, 3'-O-Me-m⁷G(5')ppp (5')C, 3'-O-Me-m⁷G(5')ppp(5')A, m73'd (5')ppp(5')G, m73'd (5')ppp(5')C, m73'd (5')ppp(5')A and their tetraphosphate derivatives) (see, e.g., Jemielity et al., RNA, 9:1108-1122 (2003)).

In particular embodiments, mRNAs encoding a homing endonuclease variant or megaTAL comprise a 5' cap that is a 7-methyl guanylate ("m⁷G") linked via a triphosphate bridge to the 5'-end of the first transcribed nucleotide, resulting in m⁷G(5')ppp(5') N, where N is any nucleoside.

In some embodiments, mRNAs encoding a homing endonuclease variant or megaTAL comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m⁷G(5')ppp (5')G cap.

In one embodiment, an mRNA comprises an ARCA cap.

In particular embodiments, an mRNA encoding a homing endonuclease variant or megaTAL comprises one or more modified nucleosides.

In one embodiment, an mRNA encoding a homing endonuclease variant or megaTAL comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA encoding a homing endonuclease variant or megaTAL comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA encoding a homing endonuclease variant or megaTAL comprises one or more modified nucleosides selected from the group consisting of: 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA encoding a homing endonuclease variant or megaTAL comprises one or more modified nucleosides selected from the group consisting of: 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA encoding a homing endonuclease variant or megaTAL comprises one or more modified nucleosides selected from the group consisting of: inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA encoding a homing endonuclease variant or megaTAL comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' AGTCATG3' is 3'TCAGTAC 5'. The latter sequence is often written as the reverse complement with the 5' end on the left and the 3' end on the right, 5' CATGACT3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector including but not limited to an origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions, which interact with host cellular proteins to carry out transcription and translation. Such elements may vary in their strength and specificity. Depending on the vector system and host utilized, any number of suitable transcription and translation elements, including ubiquitous promoters and inducible promoters may be used.

The term "operably linked" refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin poly A sequence (rβgpA), variants thereof, or another suitable heterologous or endogenous polyA sequence known in the art. In particular embodiments, the poly(A) sequence is synthetic.

In particular embodiments, polynucleotides encoding one or more nuclease variants, megaTALs, end-processing enzymes, or fusion polypeptides may be introduced into a cell by both non-viral and viral methods.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid: nucleic acid conjugates, naked DNA, artificial virions, DEAE-dextran-mediated transfer, gene gun, and heat-shock.

Illustrative examples of viral vector systems suitable for use in particular embodiments contemplated herein include, but are not limited to adeno-associated virus (AAV), retrovirus, e.g., lentivirus, herpes simplex virus, adenovirus, and vaccinia virus vectors.

F. Compositions and Formulations

The compositions contemplated in particular embodiments may comprise one or more homing endonuclease variants and megaTALs engineered to increase thermostability and/or enzymatic activity, polynucleotides, vectors comprising same, and genome editing compositions and genome edited cell compositions, as contemplated herein. The genome editing compositions and methods contemplated in particular embodiments are useful for editing a target site in the human genome in a cell or a population of cells.

An "isolated cell" refers to a non-naturally occurring cell, e.g., a cell that does not exist in nature, a modified cell, an engineered cell, a recombinant cell etc., that has been obtained from an in vivo tissue or organ and is substantially free of extracellular matrix.

As used herein, the term "population of cells" refers to a plurality of cells that may be made up of any number and/or combination of homogenous or heterogeneous cell types.

In particular embodiments, a genome editing composition is used to edit a target site in an embryonic stem cell or an adult stem or progenitor cell.

In particular embodiments, a genome editing composition is used to edit a target site in a stem or progenitor cell selected from the group consisting of: mesodermal stem or progenitor cells, endodermal stem or progenitor cells, and ectodermal stem or progenitor cells. Illustrative examples of mesodermal stem or progenitor cells include but are not limited to bone marrow stem or progenitor cells, umbilical cord stem or progenitor cells, adipose tissue derived stem or progenitor cells, hematopoietic stem or progenitor cells (HSPCs), mesenchymal stem or progenitor cells, muscle stem or progenitor cells, kidney stem or progenitor cells, osteoblast stem or progenitor cells, chondrocyte stem or progenitor cells, and the like. Illustrative examples of ectodermal stem or progenitor cells include but are not limited to neural stem or progenitor cells, retinal stem or progenitor cells, skin stem or progenitor cells, and the like. Illustrative examples of endodermal stem or progenitor cells include but are not limited to liver stem or progenitor cells, pancreatic stem or progenitor cells, epithelial stem or progenitor cells, and the like.

In particular embodiments, a genome editing composition is used to edit a target site in a bone cell, osteocyte, osteoblast, adipose cell, chondrocyte, chondroblast, muscle cell, skeletal muscle cell, myoblast, myocyte, smooth muscle cell, bladder cell, bone marrow cell, central nervous system (CNS) cell, peripheral nervous system (PNS) cell, glial cell, astrocyte cell, neuron, pigment cell, epithelial cell, skin cell, endothelial cell, vascular endothelial cell, breast cell, colon cell, esophagus cell, gastrointestinal cell, stomach cell, colon cell, head cell, neck cell, gum cell, tongue cell, kidney cell, liver cell, lung cell, nasopharynx cell, ovary cell, follicular cell, cervical cell, vaginal cell, uterine cell, pancreatic cell, pancreatic parenchymal cell, pancreatic duct cell, pancreatic islet cell, prostate cell, penile cell, gonadal cell, testis cell, hematopoietic cell, lymphoid cell, or myeloid cell.

In a preferred embodiment, a genome editing composition is used to edit a target site in hematopoietic cells, e.g., hematopoietic stem cells, hematopoietic progenitor cells, CD34+ cells, immune effector cells, T cells, NKT cells, NK cells and the like.

In various embodiments, the compositions contemplated herein comprise I-OnuI HE variant engineered to increase thermostability and/or enzymatic activity, and optionally an end-processing enzyme, e.g., a 3'-5' exonuclease (Trex2). The I-OnuI HE variant may be in the form of an mRNA that is introduced into a cell via polynucleotide delivery methods disclosed supra, e.g., electroporation, lipid nanoparticles, etc. In one embodiment, a composition comprising an mRNA encoding an I-OnuI HE variant or megaTAL, and optionally a 3'-5' exonuclease, is introduced in a cell via polynucleotide delivery methods disclosed supra. The composition may be used to generate a genome edited cell or population of genome edited cells by error prone NHEJ.

In various embodiments, the compositions contemplated herein comprise a donor repair template. The composition may be delivered to a cell that expresses or will express an I-OnuI HE variant, and optionally an end-processing enzyme. In one embodiment, the composition may be delivered to a cell that expresses or will express an I-OnuI HE variant or megaTAL, and optionally a 3'-5' exonuclease. Expression of the gene editing enzymes in the presence of the donor repair template can be used to generate a genome edited cell or population of genome edited cells by HDR.

In particular embodiments, a composition comprises a cell containing one or more homing endonuclease variants and megaTALs engineered to increase thermostability and/or enzymatic activity, polynucleotides, vectors comprising same. In particular embodiments, the cells may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

In particular embodiments, the compositions contemplated herein comprise a population of cells, an I-OnuI HE variant, and optionally, a donor repair template. In particular embodiments, the compositions contemplated herein comprise a population of cells, an I-OnuI HE variant, an end-processing enzyme, and optionally, a donor repair template. The I-OnuI HE and/or end-processing enzyme may be in the form of an mRNA that is introduced into the cell via polynucleotide delivery methods disclosed supra.

In particular embodiments, the compositions contemplated herein comprise a population of cells, an I-OnuI HE variant or megaTAL engineered to increase thermostability and/or activity of the enzyme, and optionally, a donor repair template. In particular embodiments, the compositions contemplated herein comprise a population of cells, an I-OnuI HE variant or megaTAL, a 3'-5' exonuclease, and optionally, a donor repair template. The I-OnuI HE variant, megaTAL, and/or 3'-5' exonuclease may be in the form of an mRNA that is introduced into the cell via polynucleotide delivery methods disclosed supra.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Identification of Amino Acid Positions in a LADLIDADG Homing Endonuclease that Increase Thermostability A yeast surface display assay was used to identify mutations that increase the thermostability of LAGLIDADG homing endonucleases. First, the stability of I-OnuI (e.g., SEQ ID NO: 1) and engineered nucleases (e.g., SEQ ID NOs: 6 and 7) was measured. After nuclease surface expression was induced in the yeast, each yeast population was subjected to heat shock at multiple temperatures for 15 minutes, and the percent of nuclease expressing cells still able to cleave its DNA target was measured by flow cytometry. This assay generates a standard protein melt curve with an associated $TM_{50}$ value for each endonuclease. FIG. 1.

Figure 2:
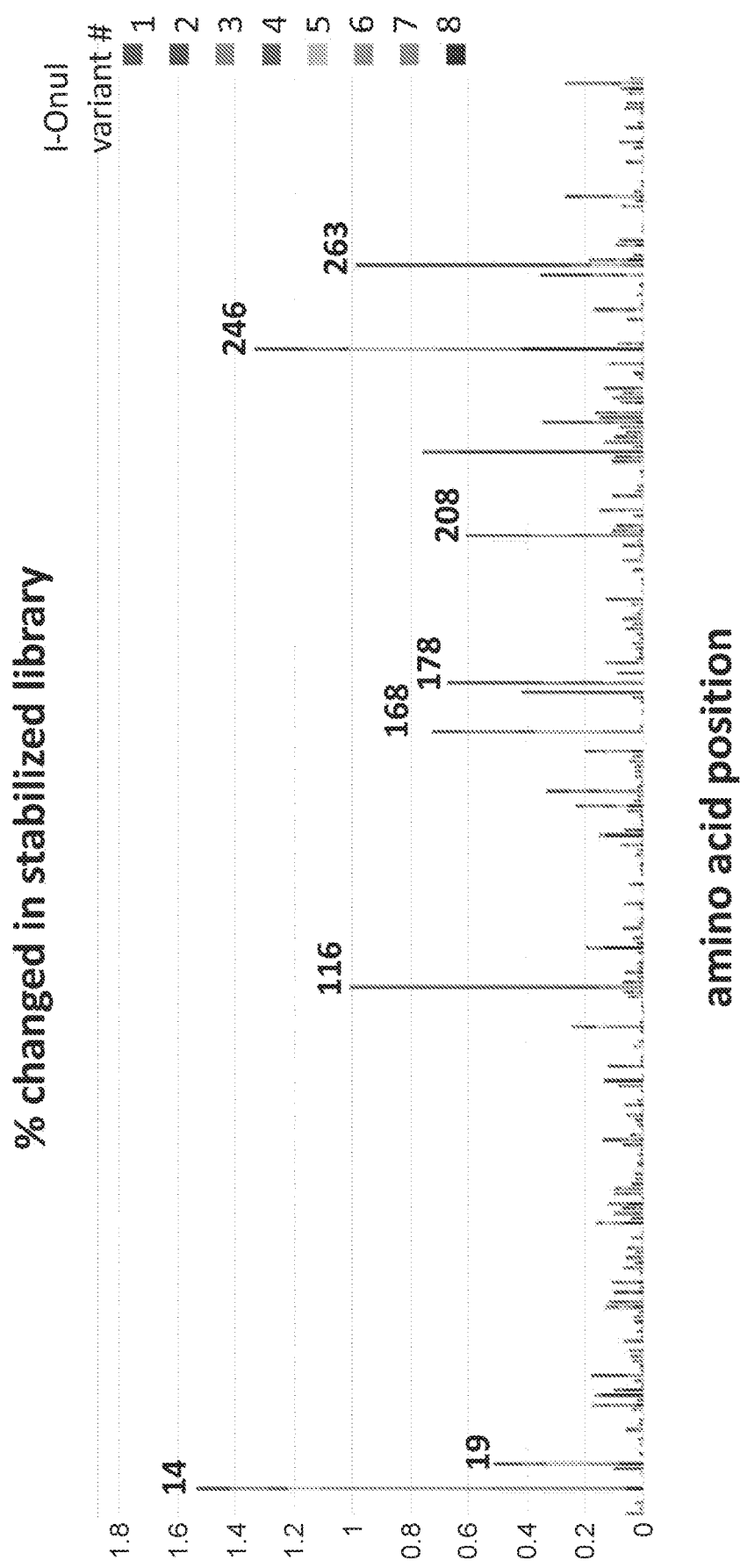
FIG. 2 shows a stacked bar graph of the percent change at each position from eight I-OnuI LHE variants randomly mutagenized and sorted for greater stability. The positions with a percent change greater than 2 standard deviations above the average are identified.
Figure 3A:
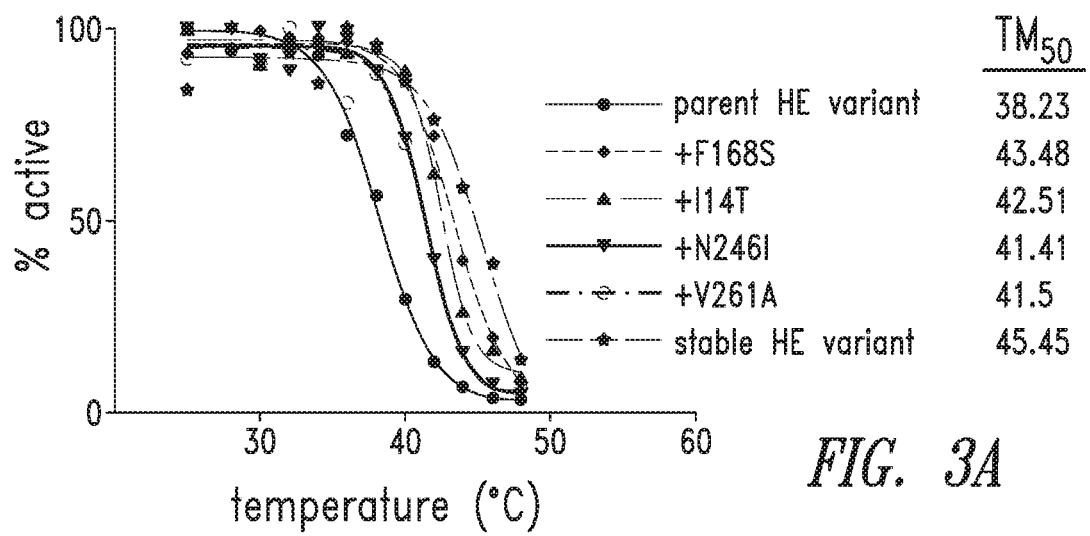
FIG. 3A shows the melt curves for a parent BCL11A I-OnuI LHE variant endonuclease, a BCL11A I-OnuI LHE variant endonuclease with individual stabilizing point mutations (F168S, I14T, N246I, V261A), and a BCL11A I-OnuI LHE variant that was randomly mutagenized (stable HE variant).

To identify mutations that lead to increased stability, multiple I-OnuI derived homing endonucleases were subjected to random mutagenesis via PCR over the entire open reading frame. These mutant libraries were expressed in yeast and sorted for active nuclease activity after heat shock at or above the $TM_{50}$ of the library. After two rounds of sorting, HE variants were sequenced with either PacBio or Sanger sequencing to determine the identity and frequency of mutations at each position. The cumulative mutation frequencies are shown in FIG. 2 as a stacked bar graph, and top mutations at each position are shown in Table 2. FIG. 3A shows the thermostability on a parent I-OnuI HE variant targeting BCL11A (SEQ ID NO 8), I-OnuI HE variants with single amino acid substitutions and their impact on thermostability (SEQ ID NOs: 9-12), and a representative I-OnuI HE variant (SEQ ID NO 13) generated from random mutagenesis that has a slightly higher overall $TM_{50}$ than the individual variants. FIG. 3A Example 2

Combinatorial I-OnuI HE Stabilizing Mutations Increase Thermostability

Figure 3B:
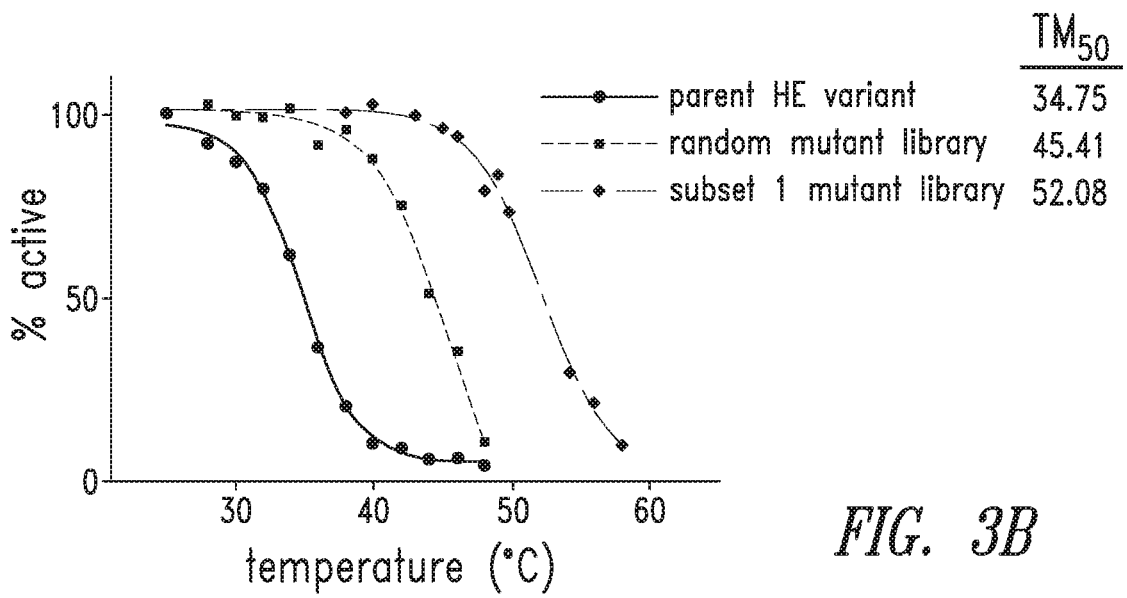
FIG. 3B shows the melt curves for a parent BCL11A I-OnuI LHE variant endonuclease, a post-sorted population of BCL11A I-OnuI LHE variants generated from a randomly mutagenized library, and a post-sorted population of BCL11A I-OnuI LHE variants generated from focused mutagenesis of amino acid positions that influence stability.
Figure 3C:
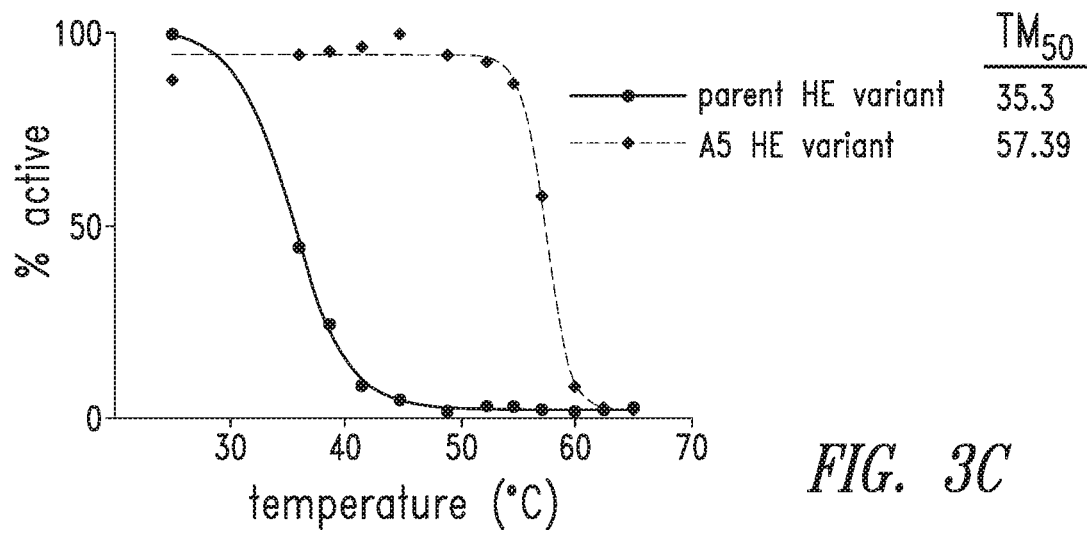
FIG. 3C shows the melt curves for a parent BCL11A I-OnuI LHE variant endonuclease and a BCL11A I-OnuI LHE A5 thermostability variant.

To further increase I-OnuI HE variant thermostability, the most frequently mutated amino acid positions were combined in a single library. Starting with BCL11A I-OnuI HE variant (SEQ ID NO 8), residues 14, 153, 156, 168, 178, 208, 261 and 300 were mutated using degenerate codons and PCR (subset 1 mutant library). Sorting of this library at a relatively permissive temperature of 46° C. resulted in a population of variants that were 10° C. more stable than the products from a random mutant library (FIG. 3B). One representative BCL11A I-OnuI HE variant from the subset 1 mutant library (A5, SEQ ID NO 14) showed an unexpected 22° C. increase in thermostability compared to the parent I-OnuI HE variant (FIG. 3C). Combinatorial mutations derived from either random mutagenesis or directed mutagenesis increase I-Onu HE variant thermostability.

Example 3

Figure 4A:
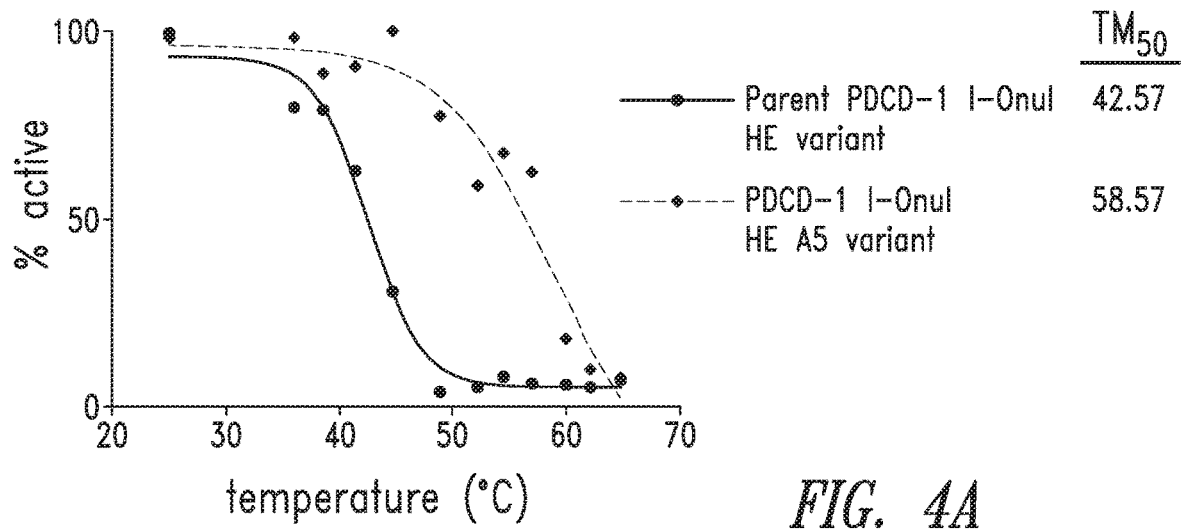
FIG. 4A-4C shows that the A5 thermostability enhancing mutations can stabilize I-OnuI LHE variants that target PCDC-1 (FIG. 4A), CBLB (FIG. 4B), and TCRα (FIG. 4C).
Figure 4B:
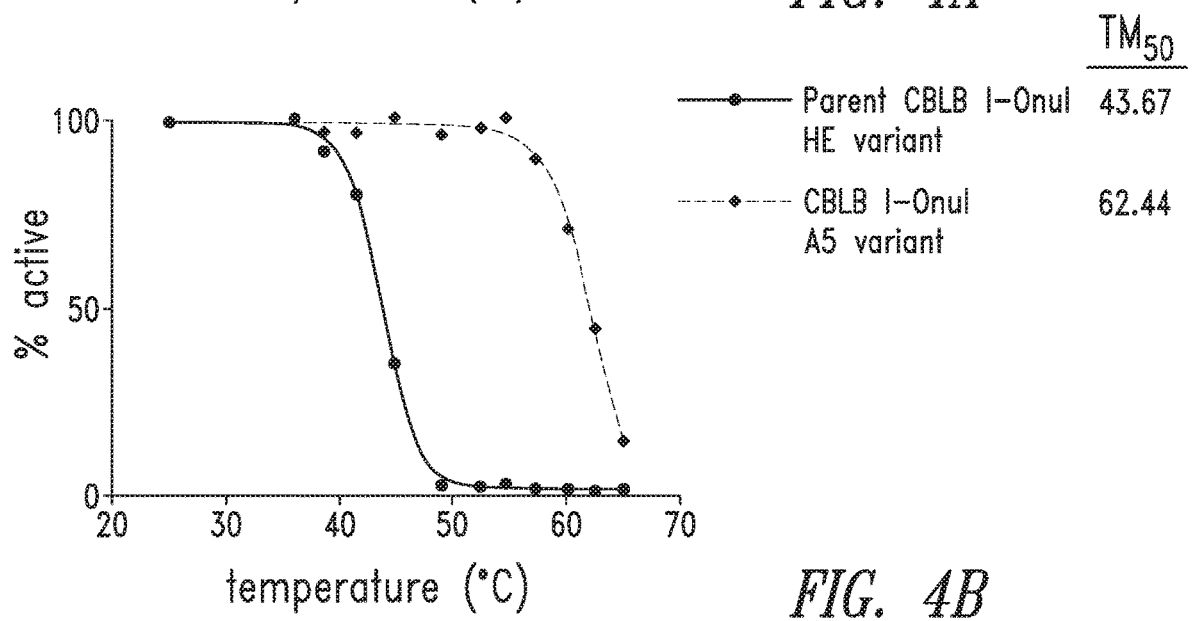
Figure 4C:
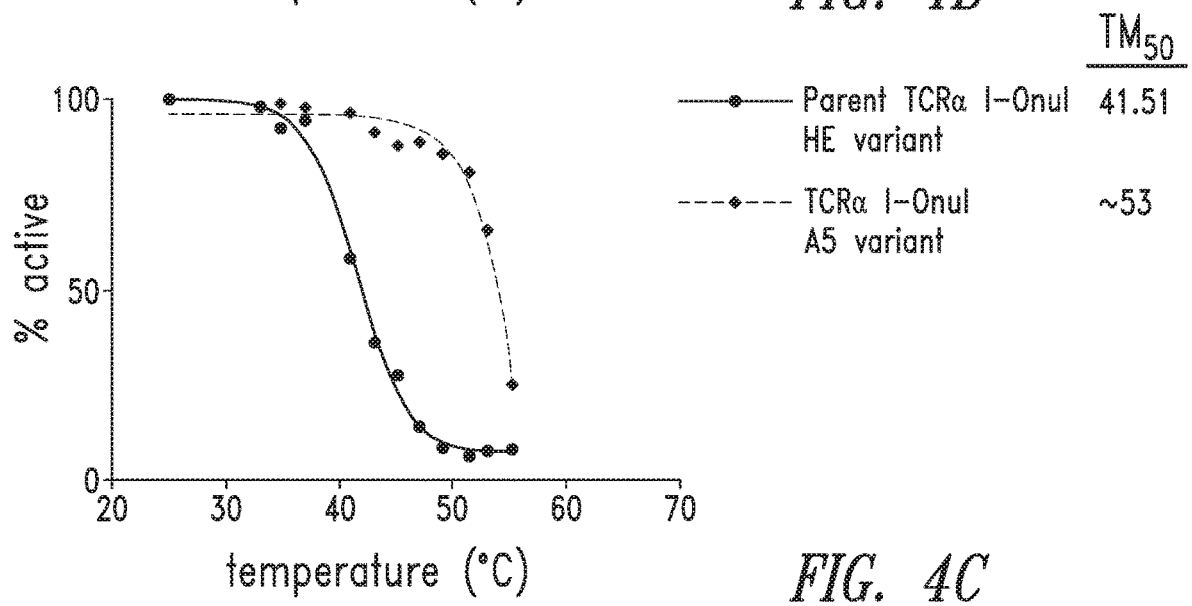

Mutations that Increase Thermostability can be Transferred Between I-OnuI HE Variants To determine if stabilizing mutations are unique to each reprogrammed I-OnuI HE variant or whether stabilizing mutations can be transferred between enzymes, the mutations from the BCL11A A5 I-OnuI HE variant (SEQ ID NO: 14) were transferred to I-OnuI HE variants that target PDCD-1 (SEQ ID NO: 15), TCRα (SEQ ID NO: 6), or CBLB (SEQ ID NO: 7). With these mutations, the $TM_{50}$ of an I-OnuI HE variant that targets the human PDCD-1 gene was increased by 16° C. (SEQ ID NO: 16), the $TM_{50}$ of an I-OnuI HE variant that targets the human TCRα gene was increased by ~14° C. (SEQ ID NO: 17), and the $TM_{50}$ of an I-OnuI HE variant that targets the human CBLB gene was increased by 19° C. (SEQ ID NO: 18). FIGS. 4A-4C. Mutations that increase thermostability were transferrable among different I-OnuI HE variants.

Example 4

Figure 5A:
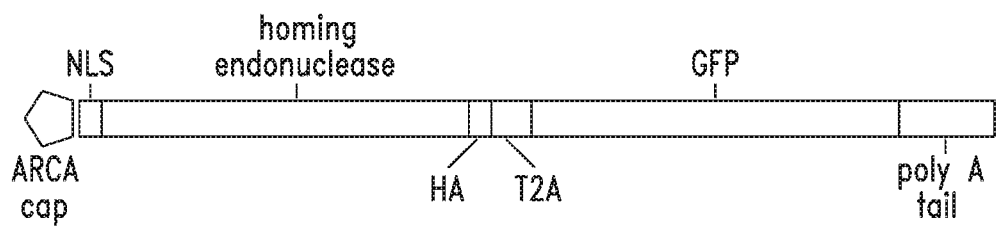
FIG. 5A shows a cartoon of a reporter construct used for assessing homing endonuclease stability.

Increased Thermostability Increases the Duration of I-OnuI HE Variant Expression I-OnuI HE variant thermostability was also assessed by measuring expression of the enzymes in 293T cells. Briefly, each I-OnuI HE variant was formatted as an mRNA with a c-terminal HA tag followed by T2A GFP to track mRNA transfection efficiency (FIG. 5A). mRNA was prepared by in vitro transcription and co-transcriptionally capped with Anti-Reverse Cap Analog and enzymatically polyadenylated with poly(A) polymerase. The mRNA was purified and equal amounts electroporated into 293T cells (protein SEQ ID NOs 2,8,14: mRNA SEQ ID NOs: 19-21). At each time point cells were run on a cytometer to measure GFP expression, as well as lysed and frozen for western blot analysis.

Figure 5B:
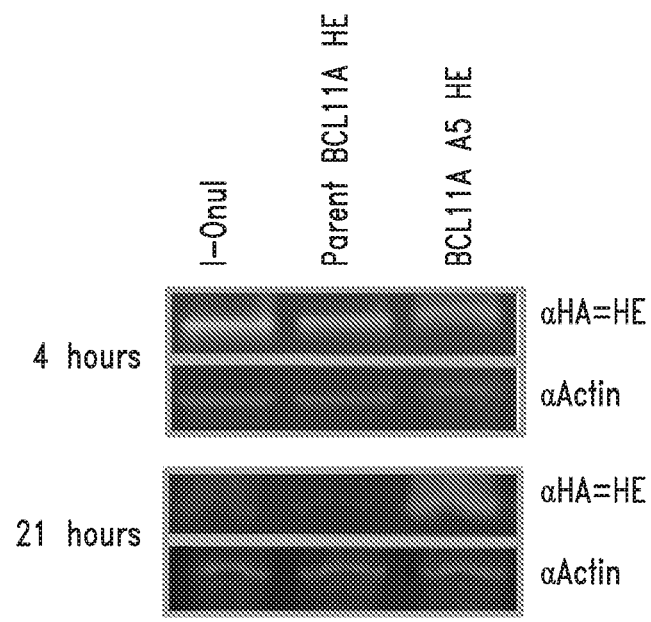
FIG. 5B shows a western blot comparing protein expression of I-OnuI, a parental BCL11A I-OnuI LHE variant, and the BCL11A I-OnuI LHE A5 variant.
Figure 5C:
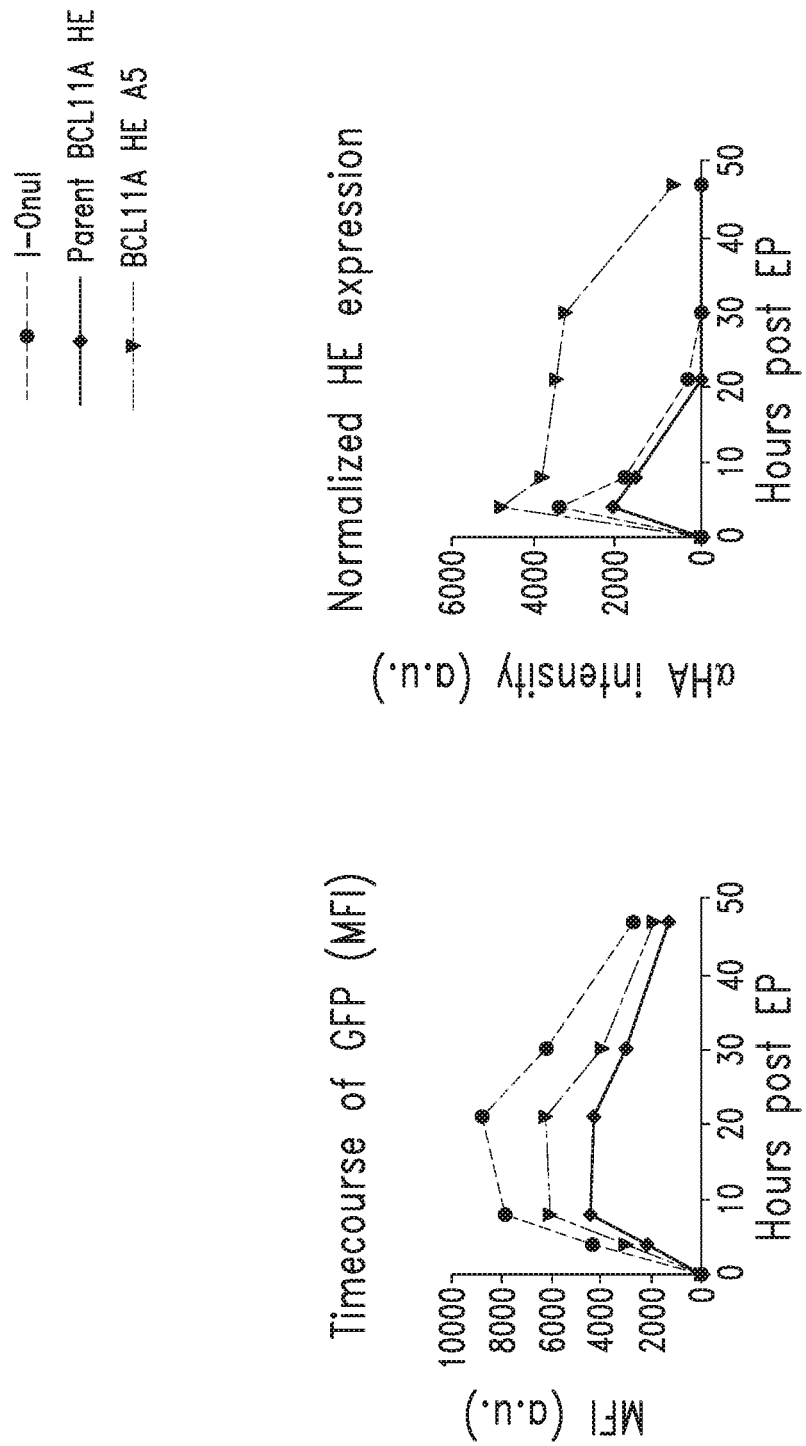
FIG. 5C shows a timecourse of expression of a GFP reporter compared to I-OnuI, a parental BCL11A I-OnuI LHE variant, and the BCL11A I-OnuI LHE A5 variant.

The dynamics for GFP protein expression were similar for each polycistronic mRNA; but the amount of HA tagged HE protein varied (FIGS. 5B and 5C). Four hours after electroporation, the amount of stabilized BCL11A A5 HE protein was significant higher compared to the amount of parent BCL11A HE protein, when normalized to the actin loading control. Moreover, at the later time points, e.g., 21 hours, the amount of parent BCL11A HE protein was undetectable; in contrast, the BCL11A A5 HE variant was still near its peak expression levels. Overall, the stabilized BCL11A A5 HE variant was present in the cells for almost twice as long as the parent HE.

Example 5

I-OnuI HE Variant Engineered to Increase Thermostability Shows Increase Catalytic Activity The effects of the stabilizing mutations on PDCD-1 editing was measured by comparing editing rates of a parental megaTAL that lacks the stabilizing mutations (SEQ ID NO: 22) with a megaTAL comprising stabilizing mutations (SEQ ID NO: 23). megaTAL mRNA was prepared by in vitro transcription, co-transcriptionally capped with Anti-Reverse Cap Analog (ARCA) and enzymatically polyadenylated with poly(A) polymerase. Purified mRNA was used to measure PDCD-1 editing efficiency in primary human T cells.

Figure 6:
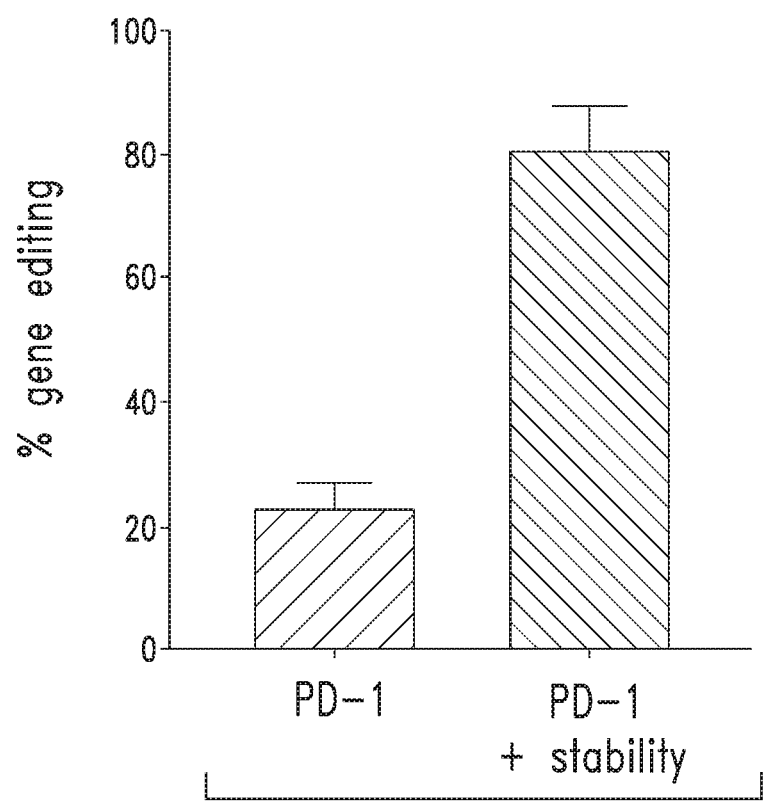
FIG. 6 shows that increasing thermostability of a PDCD-1 megaTAL significantly increases editing activity compared to its parent PDCD-1 megaTAL.

Primary human peripheral blood mononuclear cells (PBMCs) from two donors were activated with anti-CD3 and anti-CD28 antibodies and cultured in the presence of 250U/mL IL-2. At 3 days post-activation cells were electroporated with megaTAL mRNA. Transfected T cells were expanded for an additional 7-10 days and editing efficiency was measured using sequencing across the PDCD-1 target site and Tracking of Indels by Decomposition (TIDE, see Brinkman et al., 2014) (FIG. 6). Without the stabilizing mutations, the PDCD-1 megaTAL showed low levels of editing (<20%); the stabilized PDCD-1 megaTAL increased editing activity to nearly 80%.

In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

What is claimed is:

1. An I-OnuI homing endonuclease (HE) variant comprising at least 97% sequence identity to a reference I-OnuI comprising any one of SEQ ID NOs: 1-8 and 15, further comprising at least four amino acid substitutions relative to the reference I-OnuI HE that increase the thermostability of the I-OnuI HE variant compared to the reference I-OnuI HE, and wherein the at least four of the amino acid substitutions consist of:
   (i) amino acid substitutions at the following amino acid positions: 14, 19, 168, 208, and 246, in reference to SEQ ID NO: 1;
   (ii) three of more amino acid substitutions at an amino acid position selected from the group consisting of: 14, 19, 116, 156, 168, 176, 208, 231, 246, 261, 263, 277, and 300, in reference to SEQ ID NO: 1; and one or more amino acid substitutions at an amino acid position selected from the group consisting of: 31, 33, 52, 97, 124, 147, 153, 209, 264, and 268, in reference to SEQ ID NO: 1;
   (iii) five or more amino acid substitutions at an amino acid position selected from the group consisting of: 14, 19, 116, 156, 168, 176, 208, 231, 246, 261, 263, 277, and 300, in reference to SEQ ID NO: 1; and/or
   (iv) five or more amino acid substitutions at an amino acid position selected from the group consisting of: 14, 19, 116, 156, 168, 176, 208, 231, 246, 261, 263, 277, and 300, in reference to SEQ ID NO: 1; and one or more amino acid substitutions at an amino acid position selected from the group consisting of: 31, 33, 52, 97, 124, 147, 153, 209, 264, and 268, in reference to SEQ ID NO:1.

2. The I-OnuI HE variant of claim 1, wherein the I-OnuI HE variant has a $TM_{50}$ of:
   (a) at least 10° C. higher than the $TM_{50}$ of the reference I-OnuI HE;
   (b) at least 15° C. higher than the $TM_{50}$ of the reference I-OnuI HE;
   (c) at least 20° C. higher than the $TM_{50}$ of the reference I-OnuI HE; or
   (d) at least 25° C. higher than the $TM_{50}$ of the reference I-OnuI HE.

3. The I-OnuI HE variant of claim 1, wherein the I-OnuI HE variant targets a site in a gene selected from the group consisting of: HBA, HBB, HBG1, HBG2, BCL11A, PCSK9, TCRA, TCRB, B2M, HLA-A, HLA-B, HLA-C, HLA-E, HLA-F, HLA-G, CIITA, AHR, PD-1, CTLA4, TIGIT, TGFβR2, LAG-3, TIM-3, BTLA, IL4R, IL6R, CXCR1, CXCR2, IL10R, IL13Rα2, TRAILR1, RCAS1R, and FAS.

4. The I-OnuI HE variant of claim 1, wherein:
   (a) the amino acid at position 14 is selected from the group consisting of: T, V, S, N, M, K, F, and D;
   (b) the amino acid at position 19 is selected from the group consisting of: C, D, I, L, S, T, and V;
   (c) the amino acid at position 116 is selected from the group consisting of: F, D, A, L, and I;
   (d) the amino acid at position 168 is selected from the group consisting of: G, H, Y, I, V, P, L, and S;
   (e) the amino acid at position 208 is selected from the group consisting of: N, V, Y, and E;
   (f) the amino acid at position 246 is selected from the group consisting of: H, I, D, R, S, T, V, Y, and K; and/or
   (g) the amino acid at position 263 is selected from the group consisting of: H, F, P, T, V, and R.

5. The I-OnuI HE variant of claim 1, wherein:
   (a) the amino acid at position 14 is selected from the group consisting of: T and V;
   (b) the amino acid at position 19 is selected from the group consisting of: T and V;
   (c) the amino acid at position 116 is selected from the group consisting of: L and I;
   (d) the amino acid at position 168 is selected from the group consisting of: G, L, and S;
   (e) the amino acid at position 208 is E;
   (f) the amino acid at position 246 is K; and/or
   (g) the amino acid at position 263 is selected from the group consisting of: H and R.

6. The I-OnuI HE variant of claim 1, wherein:
   (a) the amino acid at position 156 is selected from the group consisting of: N, Q, R, T, V, I, and E;
   (b) the amino acid at position 176 is selected from the group consisting of: P, N, and A;
   (c) the amino acid at position 231 is selected from the group consisting of: D, K, V, and G;
   (d) the amino acid at position 261 is selected from the group consisting of: M, D, G, I, L, S, T, and A;
   (e) the amino acid at position 277 is selected from the group consisting of: A, D, G, Q, V, and K; and/or
   (f) the amino acid at position 300 is selected from the group consisting of: S, V, D, C, and R.

7. The I-OnuI HE variant of claim 1, wherein:
(a) the amino acid at position 156 is selected from the group consisting of: R, I, and E;
(b) the amino acid at position 176 is A;
(c) the amino acid at position 231 is selected from the group consisting of: K and G;
(d) the amino acid at position 261 is selected from the group consisting of: M and A;
(e) the amino acid at position 277 is K; and/or
(f) the amino acid at position 300 is R.

8. The I-OnuI HE variant of claim 1, wherein:
(a) the amino acid at position 31 is selected from the group consisting of: D, H, I, R, K, S, T, and Y;
(b) the amino acid at position 33 is selected from the group consisting of: D, G, H, I, K, S, T, and Y;
(c) the amino acid at position 52 is selected from the group consisting of: Q, R, T, Y, N, E, and M;
(d) the amino acid at position 97 is selected from the group consisting of: F, N, and H;
(e) the amino acid at position 124 is selected from the group consisting of: E, N, R, and T;
(f) the amino acid at position 147 is selected from the group consisting of: E, I, N, R, and T;
(g) the amino acid at position 153 is selected from the group consisting of: D, H, K, T, Y, S, V, and N;
(h) the amino acid at position 209 is selected from the group consisting of: E, M, N, Q, and R;
(i) the amino acid at position 264 is selected from the group consisting of: A, D, G, K, Q, R, and V; and/or
(j) the amino acid at position 268 is selected from the group consisting of: A, E, G, H, N, V, and Y.

9. The I-OnuI HE variant of claim 1, wherein:
(a) the amino acid at position 31 is K;
(b) the amino acid at position 33 is K;
(c) the amino acid at position 52 is M;
(d) the amino acid at position 97 is F;
(e) the amino acid at position 124 is N;
(f) the amino acid at position 147 is I;
(g) the amino acid at position 153 is selected from the group consisting of: D, V, and N;
(h) the amino acid at position 209 is R;
(i) the amino acid at position 264 is K; and/or
(j) the amino acid at position 268 is N.

10. The I-OnuI HE variant of claim 1, wherein the at least four amino acid substitutions is five or more amino acid substitutions.

11. The I-OnuI HE variant of claim 1, wherein the amino acid at position 108 is selected from the group consisting of: K and M.

12. The I-OnuI HE variant of claim 1, wherein the amino acid at position 108 is selected from the group consisting of: E, N, Q, R, T, and V.

13. An I-OnuI homing endonuclease (HE) variant comprising at least 97% sequence identity to a reference I-OnuI HE comprising any one of SEQ ID NOs: 1-8 and 15, further comprising at least four amino acid substitutions relative to the reference I-OnuI HE, that increase the thermostability of the I-OnuI HE variant compared to the reference I-OnuI HE, and wherein the at least four of the amino acid substitutions are selected from amino acid substitutions at the following amino acid positions: 14, 19, 31, 33, 52, 97, 116, 124, 147, 153, 156, 168, 176, 208, 209, 231, 246, 261, 263, 264, 268, 277, and 300, in reference to SEQ ID NO: 1; and wherein:
(a) the amino acid at position 14 is selected from the group consisting of T, V, S, N, M, K, F, and D;
(b) the amino acid at position 19 is selected from the group consisting of C, D, I, L, S, T, and V;
(c) the amino acid at position 31 is selected from the group consisting of: D, H, I, R, K, S, T, and Y;
(d) the amino acid at position 33 is selected from the group consisting of: D, G, H, I, K, S, T, and Y;
(e) the amino acid at position 52 is selected from the group consisting of: Q, R, T, Y, N, E, and M;
(f) the amino acid at position 97 is selected from the group consisting of: F, N, and H;
(g) the amino acid at position 116 is selected from the group consisting of: F, D, A, L, and I;
(h) the amino acid at position 124 is selected from the group consisting of: E, N, R, and T;
(i) the amino acid at position 147 is selected from the group consisting of: E, I, N, R, and T;
(j) the amino acid at position 153 is selected from the group consisting of: D, H, K, T, Y, S, V, and N;
(k) the amino acid at position 156 is selected from the group consisting of: N, Q, R, T, V, I, and E;
(l) the amino acid at position 168 is selected from the group consisting of: G, H, Y, I, V, P, L, and S;
(m) the amino acid at position 176 is selected from the group consisting of: P, N, and A;
(n) the amino acid at position 208 is selected from the group consisting of: N, V, Y, and E;
(o) the amino acid at position 209 is selected from the group consisting of E, M, N, Q, and R;
(p) the amino acid at position 231 is selected from the group consisting of: D, K, V, and G;
(q) the amino acid at position 246 is selected from the group consisting of: H, I, D, R, S, T, V, Y, and K;
(r) the amino acid at position 261 is selected from the group consisting of: M, D, G, I, L, S, T, and A;
(s) the amino acid at position 263 is selected from the group consisting of: H F P T V and R;
(t) the amino acid at position 264 is selected from the group consisting of: A D, G, K, Q, R, and V;
(u) the amino acid at position 268 is selected from the group consisting of: A E, G, H, N, V, and Y;
(v) the amino acid at position 277 is selected from the group consisting of: A D, G, Q, V, and K; and/or
(w) the amino acid at position 300 is selected from the group consisting of: S, V, D, C, and R.

14. The I-OnuI HE variant of claim 13, wherein:
(a) the amino acid at position 14 is selected from the group consisting of: T and V;
(b) the amino acid at position 19 is selected from the group consisting of: T and V;
(c) the amino acid at position 31 is K;
(d) the amino acid at position 33 is K;
(e) the amino acid at position 52 is M;
(f) the amino acid at position 97 is F;
(g) the amino acid at position 116 is selected from the group consisting of: L and I;
(h) the amino acid at position 124 is N;
(i) the amino acid at position 147 is I;
(j) the amino acid at position 153 is selected from the group consisting of: D, V, and N;
(k) the amino acid at position 156 is selected from the group consisting of: I, R, and E;
(l) the amino acid at position 168 is selected from the group consisting of: G, L, and S;
(m) the amino acid at position 176 is A;
(n) the amino acid at position 208 is E;
(o) the amino acid at position 209 is R;
(p) the amino acid at position 231 is selected from the group consisting of: K and G;
(q) the amino acid at position 246 is K;

(r) the amino acid at position 261 is selected from the group consisting of: M and A;
(s) the amino acid at position 263 is selected from the group consisting of: H and R;
(t) the amino acid at position 264 is K;
(u) the amino acid at position 268 is N;
(v) the amino acid at position 277 is K; and/or
(w) the amino acid at position 300 is R.

15. The I-OnuI HE variant of claim 13, wherein the I-OnuI HE variant comprises five or more amino acid substitutions.

16. The I-OnuI HE variant of claim 13, wherein the at least four of the amino acid substitutions are selected from amino acid substitutions at the following amino acid positions: 14, 19, 31, 116, 153, 156, 168, 176, 208, 246, 261, 263, and 300.

17. The I-OnuI HE variant of claim 13, wherein the at least four of the amino acid substitutions are selected from amino acid substitutions at the following amino acid positions: 14, 153, 156, 168, 176, 246, 261, 263, and 300.

18. The I-OnuI HE variant of claim 17, wherein the amino acid at selected position 14 is T, the amino acid at selected position 153 is V, the amino acid at selected position 156 is R, the amino acid at selected position 168 is G, the amino acid at selected position 176 is A, the amino acid at selected position 246 is I, the amino acid at selected position 261 is M, the amino acid at selected position 263 is H, and the amino acid at selected position 300 is R.

19. The I-OnuI HE variant of claim 13 comprising an amino acid sequence selected from the group consisting of SEQ ID NO: 14, SEQ ID NO: 16, SEQ ID NO: 17, and SEQ ID NO: 18.

20. The I-OnuI HE variant of claim 13 comprising an amino acid sequence set forth in SEQ ID NO: 18.

* * * * *

SEQUENCE LISTING

<160> NUMBER OF SEQ ID NOS: 59

<210> SEQ ID NO 1
<211> LENGTH: 303
<212> TYPE: PRT
<213> ORGANISM: Ophiostoma novo-ulmi

```
<400> SEQUENCE: 1

Met Ala Tyr Met Ser Arg Arg Glu Ser Ile Asn Pro Trp Ile Leu Thr
 1               5                   10                  15

Gly Phe Ala Asp Ala Glu Gly Ser Phe Leu Leu Arg Ile Arg Asn Asn
             20                  25                  30

Asn Lys Ser Ser Val Gly Tyr Ser Thr Glu Leu Gly Phe Gln Ile Thr
         35                  40                  45

Leu His Asn Lys Asp Lys Ser Ile Leu Glu Asn Ile Gln Ser Thr Trp
     50                  55                  60

Lys Val Gly Val Ile Ala Asn Ser Gly Asp Asn Ala Val Ser Leu Lys
 65                  70                  75                  80

Val Thr Arg Phe Glu Asp Leu Lys Val Ile Asp His Phe Glu Lys
                 85                  90                  95

Tyr Pro Leu Ile Thr Gln Lys Leu Gly Asp Tyr Met Leu Phe Lys Gln
                100                 105                 110

Ala Phe Cys Val Met Glu Asn Lys Glu His Leu Lys Ile Asn Gly Ile
            115                 120                 125

Lys Glu Leu Val Arg Ile Lys Ala Lys Leu Asn Trp Gly Leu Thr Asp
        130                 135                 140

Glu Leu Lys Lys Ala Phe Pro Glu Ile Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 2
<211> LENGTH: 303
<212> TYPE: PRT
<213> ORGANISM: Ophiostoma novo-ulmi

<400> SEQUENCE: 2

Met Ala Tyr Met Ser Arg Arg Glu Ser Ile Asn Pro Trp Ile Leu Thr
 1               5                   10                  15

Gly Phe Ala Asp Ala Glu Gly Ser Phe Leu Leu Arg Ile Arg Asn Asn
             20                  25                  30

Asn Lys Ser Ser Val Gly Tyr Ser Thr Glu Leu Gly Phe Gln Ile Thr
         35                  40                  45

Leu His Asn Lys Asp Lys Ser Ile Leu Glu Asn Ile Gln Ser Thr Trp
     50                  55                  60
```

-continued

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
            85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 3
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(3)
<223> OTHER INFORMATION: Any amino acid or absent

<400> SEQUENCE: 3

Xaa Xaa Xaa Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
            85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile

```
            115                 120                 125
Lys Glu Leu Val Arg Ile Lys Ala Lys Leu Asn Trp Gly Leu Thr Asp
130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 4
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 4

Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
```

```
                145                 150                 155                 160
Ile Asn Lys Asn Ile Pro Asn Phe Lys Trp Leu Ala Gly Phe Thr Ser
                    165                 170                 175

Gly Glu Gly Cys Phe Phe Val Asn Leu Ile Lys Ser Lys Ser Lys Leu
                    180                 185                 190

Gly Val Gln Val Gln Leu Val Phe Ser Ile Thr Gln His Ile Lys Asp
                    195                 200                 205

Lys Asn Leu Met Asn Ser Leu Ile Thr Tyr Leu Gly Cys Gly Tyr Ile
210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                    245                 250                 255

Thr Leu Ile Gly Val Lys Leu Glu Asp Phe Glu Asp Trp Cys Lys Val
                    260                 265                 270

Ala Lys Leu Ile Glu Glu Lys Lys His Leu Thr Glu Ser Gly Leu Asp
                    275                 280                 285

Glu Ile Lys Lys Ile Lys Leu Asn Met Asn Lys Gly Arg Xaa Xaa
    290                 295                 300

<210> SEQ ID NO 5
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(8)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 5

Xaa Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Leu Leu Arg Ile Arg Asn Asn
                20                  25                  30

Asn Lys Ser Ser Val Gly Tyr Ser Thr Glu Leu Gly Phe Gln Ile Thr
                35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                    85                  90                  95

Tyr Pro Leu Ile Thr Gln Lys Leu Gly Asp Tyr Lys Leu Phe Lys Gln
                    100                 105                 110

Ala Phe Ser Val Met Glu Asn Lys Glu His Leu Lys Glu Asn Gly Ile
                    115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                    165                 170                 175

Gly Glu Gly Cys Phe Phe Val Asn Leu Ile Lys Ser Lys Ser Lys Leu
```

```
            180                 185                 190
Gly Val Gln Val Gln Leu Val Phe Ser Ile Thr Gln His Ile Lys Asp
                195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
    260                 265                 270

Ala Lys Leu Ile Glu Glu Lys His Leu Thr Glu Ser Gly Leu Asp
    275                 280                 285

Glu Ile Lys Lys Ile Lys Leu Asn Met Asn Lys Gly Arg Xaa Xaa
    290                 295                 300

<210> SEQ ID NO 6
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE variant
<220> FEATURE:
<221> NAME/KEY: MOD_RES
<222> LOCATION: (1)..(8)
<223> OTHER INFORMATION: Any amino acid or absent

<400> SEQUENCE: 6

Xaa Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Ile Leu Asp Ile Arg Asn Arg
            20                  25                  30

Asn Asn Glu Ser Asn Arg Tyr Arg Thr Ser Leu Arg Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Thr Asn Ser Ser Asp Arg Ala Val Met Leu Arg
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ala
                165                 170                 175

Gly Asp Gly His Phe Gly Val Asn Leu Lys Lys Val Lys Gly Thr Ala
            180                 185                 190

Lys Val Tyr Val Gly Leu Arg Phe Ala Ile Ser Gln His Ile Arg Asp
        195                 200                 205

Lys Asn Leu Met Asn Ser Leu Ile Thr Tyr Leu Gly Cys Gly Ser Ile
    210                 215                 220
```

```
Arg Glu Lys Asn Lys Ser Glu Phe Arg Trp Leu Glu Phe Glu Val Thr
225                 230                 235                 240

Lys Phe Ser Asp Ile Asn Asp Lys Ile Ile Pro Val Phe Gln Glu Asn
            245                 250                 255

Thr Leu Ile Gly Val Lys Leu Glu Asp Phe Glu Asp Trp Cys Lys Val
        260                 265                 270

Ala Lys Leu Ile Glu Glu Lys Lys His Leu Thr Glu Ser Gly Leu Asp
    275                 280                 285

Glu Ile Lys Lys Ile Lys Leu Asn Met Asn Lys Gly Arg
290                 295                 300
```

<210> SEQ ID NO 7
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE variant
<220> FEATURE:
<221> NAME/KEY: MOD_RES
<222> LOCATION: (1)..(8)
<223> OTHER INFORMATION: Any amino acid or absent

<400> SEQUENCE: 7

```
Xaa Xaa Xaa Xaa Xaa Xaa Xaa Ser Ile Asn Pro Trp Ile Leu Thr
1               5                   10                  15

Gly Phe Ala Asp Ala Glu Gly Cys Phe Arg Leu Asp Ile Arg Asn Ala
            20                  25                  30

Asn Asp Leu Arg Ala Gly Tyr Arg Thr Arg Leu Ala Phe Glu Ile Val
        35                  40                  45

Leu His Asn Lys Asp Lys Ser Ile Leu Glu Asn Ile Gln Ser Thr Trp
    50                  55                  60

Lys Val Gly Thr Ile Tyr Asn Ala Gly Asp Asn Ala Val Arg Leu Gln
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Leu Lys Trp Leu Ala Gly Phe Thr Ser
                165                 170                 175

Gly Asp Gly Ser Phe Val Val Glu Leu Lys Lys Arg Arg Ser Pro Val
            180                 185                 190

Lys Val Gly Val Arg Leu Arg Phe Ser Ile Thr Gln His Ile Arg Asp
        195                 200                 205

Lys Asn Leu Met Asn Ser Leu Ile Thr Tyr Leu Gly Cys Gly Arg Ile
    210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270
```

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg
    290                 295                 300

<210> SEQ ID NO 8
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE variant
<220> FEATURE:
<221> NAME/KEY: MOD_RES
<222> LOCATION: (1)..(8)
<223> OTHER INFORMATION: Any amino acid or absent

<400> SEQUENCE: 8

Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Val Leu Ser Ile Gln Asn Arg
            20                  25                  30

Asn Asp Tyr Ala Thr Gly Tyr Arg Ile His Leu Thr Phe Gln Ile Thr
            35                  40                  45

Leu His Asn Lys Asp Lys Ser Ile Leu Glu Asn Ile Gln Ser Thr Trp
    50                  55                  60

Lys Val Gly Lys Ile Asn Asn Thr Gly Asp Asn Leu Val Gln Leu Arg
65                  70                  75                  80

Val Tyr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Asp Gly Ser Phe Phe Val Arg Leu Arg Lys Ser Asn Val Asn Ala
            180                 185                 190

Arg Val Arg Val Gln Leu Val Phe Glu Ile Ser Gln His Ile Arg Asp
        195                 200                 205

Lys Asn Leu Met Asn Ser Leu Ile Thr Tyr Leu Gly Cys Gly His Ile
    210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg
    290                 295                 300

```
<210> SEQ ID NO 9
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 9

Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Val Leu Ser Ile Gln Asn Arg
            20                  25                  30

Asn Asp Tyr Ala Thr Gly Tyr Arg Ile His Leu Thr Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Asn Asn Thr Gly Asp Asn Leu Val Gln Leu Arg
65                  70                  75                  80

Val Tyr Arg Phe Glu Asp Leu Lys Val Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Ser Lys Trp Leu Ala Gly Phe Thr Ser
                165                 170                 175

Gly Asp Gly Ser Phe Phe Val Arg Leu Arg Lys Ser Asn Val Asn Ala
            180                 185                 190

Arg Val Arg Val Gln Leu Val Phe Glu Ile Ser Gln His Ile Arg Asp
        195                 200                 205

Lys Asn Leu Met Asn Ser Leu Ile Thr Tyr Leu Gly Cys Gly His Ile
    210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg
    290                 295                 300

<210> SEQ ID NO 10
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
```

<220> FEATURE:
<221> NAME/KEY: MOD_RES
<222> LOCATION: (1)..(8)
<223> OTHER INFORMATION: Any amino acid or absent

<400> SEQUENCE: 10

```
Xaa Xaa Xaa Xaa Xaa Xaa Xaa Ser Ile Asn Pro Trp Thr Leu Thr
1               5                   10                  15

Gly Phe Ala Asp Ala Glu Gly Ser Phe Val Leu Ser Ile Gln Asn Arg
            20                  25                  30

Asn Asp Tyr Ala Thr Gly Tyr Arg Ile His Leu Thr Phe Gln Ile Thr
                35                  40                  45

Leu His Asn Lys Asp Lys Ser Ile Leu Glu Asn Ile Gln Ser Thr Trp
50                  55                  60

Lys Val Gly Lys Ile Asn Asn Thr Gly Asp Asn Leu Val Gln Leu Arg
65                  70                  75                  80

Val Tyr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Asp Gly Ser Phe Phe Val Arg Leu Arg Lys Ser Asn Val Asn Ala
            180                 185                 190

Arg Val Arg Val Gln Leu Val Phe Glu Ile Ser Gln His Ile Arg Asp
        195                 200                 205

Lys Asn Leu Met Asn Ser Leu Ile Thr Tyr Leu Gly Cys Gly His Ile
210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg
290                 295                 300
```

<210> SEQ ID NO 11
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE thermostable variant
<220> FEATURE:
<221> NAME/KEY: MOD_RES
<222> LOCATION: (1)..(8)
<223> OTHER INFORMATION: Any amino acid or absent

<400> SEQUENCE: 11

Xaa Xaa Xaa Xaa Xaa Xaa Xaa Ser Ile Asn Pro Trp Ile Leu Thr
 1               5                  10                  15

Gly Phe Ala Asp Ala Glu Gly Ser Phe Val Leu Ser Ile Gln Asn Arg
             20                  25                  30

Asn Asp Tyr Ala Thr Gly Tyr Arg Ile His Leu Thr Phe Gln Ile Thr
             35                  40                  45

Leu His Asn Lys Asp Lys Ser Ile Leu Glu Asn Ile Gln Ser Thr Trp
 50                  55                  60

Lys Val Gly Lys Ile Asn Asn Thr Gly Asp Asn Leu Val Gln Leu Arg
 65                  70                  75                  80

Val Tyr Arg Phe Glu Asp Leu Lys Val Ile Ile Asp His Phe Glu Lys
                 85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
                115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Asp Gly Ser Phe Phe Val Arg Leu Arg Lys Ser Asn Val Asn Ala
                180                 185                 190

Arg Val Arg Val Gln Leu Val Phe Glu Ile Ser Gln His Ile Arg Asp
                195                 200                 205

Lys Asn Leu Met Asn Ser Leu Ile Thr Tyr Leu Gly Cys Gly His Ile
210                 215                 220

Tyr Glu Gly Asn Lys Ser Glu Arg Ser Trp Leu Gln Phe Arg Val Glu
225                 230                 235                 240

Lys Phe Ser Asp Ile Ile Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
                275                 280                 285

Glu Ile Lys Lys Ile Lys Leu Asn Met Asn Lys Gly Arg
                290                 295                 300

<210> SEQ ID NO 12
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 12

Xaa Xaa Xaa Xaa Xaa Xaa Xaa Xaa Ser Ile Asn Pro Trp Ile Leu Thr
 1               5                  10                  15

Gly Phe Ala Asp Ala Glu Gly Ser Phe Val Leu Ser Ile Gln Asn Arg
             20                  25                  30

Asn Asp Tyr Ala Thr Gly Tyr Arg Ile His Leu Thr Phe Gln Ile Thr 35                  40                  45
Leu His Asn Lys Asp Lys Ser Ile Leu Glu Asn Ile Gln Ser Thr Trp
         50                  55                  60

Lys Val Gly Lys Ile Asn Asn Thr Gly Asp Asn Leu Val Gln Leu Arg
 65                  70                  75                  80

Val Tyr Arg Phe Glu Asp Leu Lys Val Ile Asp His Phe Glu Lys
                 85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Asp Gly Ser Phe Phe Val Arg Leu Arg Lys Ser Asn Val Asn Ala
                180                 185                 190

Arg Val Arg Val Gln Leu Val Phe Glu Ile Ser Gln His Ile Arg Asp
            195                 200                 205

Lys Asn Leu Met Asn Ser Leu Ile Thr Tyr Leu Gly Cys Gly His Ile
210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
                245                 250                 255

Thr Leu Ile Gly Ala Lys Leu Glu Asp Phe Glu Asp Trp Cys Lys Val
                260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg
290                 295                 300

<210> SEQ ID NO 13
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 13

Xaa Xaa Xaa Xaa Xaa Xaa Xaa Xaa Ser Ile Asn Pro Trp Ile Leu Thr
  1               5                  10                  15

Gly Phe Ala Asp Ala Glu Gly Ser Phe Val Leu Ser Ile Gln Asn Arg
             20                  25                  30

Asn Asp Tyr Ala Thr Gly Tyr Arg Ile His Leu Thr Phe Gln Ile Thr
         35                  40                  45

Leu His Asn Lys Asp Lys Ser Ile Leu Glu Asn Ile Gln Ser Thr Trp
     50                  55                  60

Lys Val Gly Lys Ile Asn Asn Thr Gly Asp Asn Leu Val Gln Leu Arg
 65                  70                  75                  80

-continued

```
Val Tyr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Phe Lys Trp Leu Ala Gly Phe Thr Ser
                165                 170                 175

Gly Asp Gly Ser Phe Phe Val Arg Leu Arg Lys Ser Asn Val Asn Ala
            180                 185                 190

Arg Val Arg Val Arg Leu Val Phe Glu Ile Ser Gln His Val Arg Asp
        195                 200                 205

Lys Asn Leu Met Asn Ser Leu Ile Thr Tyr Leu Gly Cys Gly His Ile
    210                 215                 220

Tyr Glu Gly Asn Lys Ser Glu Arg Ser Trp Leu Gln Phe Arg Val Glu
225                 230                 235                 240

Lys Phe Ser Asp Ile Ile Asp Lys Ile Ile Pro Val Phe Gln Glu Asn
                245                 250                 255

Thr Leu Ile Gly Ala Lys His Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg
    290                 295                 300
```

<210> SEQ ID NO 14
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 14

```
Xaa Xaa Xaa Xaa Xaa Xaa Xaa Xaa Ser Ile Asn Pro Trp Thr Leu Thr
1               5                   10                  15

Gly Phe Ala Asp Ala Glu Gly Ser Phe Val Leu Ser Ile Gln Asn Arg
            20                  25                  30

Asn Asp Tyr Ala Thr Gly Tyr Arg Ile His Leu Thr Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Asn Asn Thr Gly Asp Asn Leu Val Gln Leu Arg
65                  70                  75                  80

Val Tyr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110
```

```
Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
    130                 135                 140

Glu Leu Lys Lys Ala Phe Pro Glu Val Ile Ser Arg Glu Arg Pro Leu
145                 150                 155                 160

Ile Asn Lys Asn Ile Pro Asn Gly Lys Trp Leu Ala Gly Phe Thr Ser
                165                 170                 175

Gly Asp Gly Ser Phe Phe Val Arg Leu Arg Lys Ser Asn Val Asn Ala
            180                 185                 190

Arg Val Arg Val Gln Leu Val Phe Glu Ile Ser Gln His Ile Arg Asp
    195                 200                 205

Lys Asn Leu Met Asn Ser Leu Ile Thr Tyr Leu Gly Cys Gly His Ile
210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
                245                 250                 255

Thr Leu Ile Gly Met Lys Leu Glu Asp Phe Glu Asp Trp Cys Lys Val
            260                 265                 270

Ala Lys Leu Ile Glu Glu Lys Lys His Leu Thr Glu Ser Gly Leu Asp
    275                 280                 285

Glu Ile Lys Lys Ile Lys Leu Asn Met Asn Lys Arg Arg
290                 295                 300

<210> SEQ ID NO 15
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE variant
<220> FEATURE:
<221> NAME/KEY: MOD_RES
<222> LOCATION: (1)..(8)
<223> OTHER INFORMATION: Any amino acid or absent

<400> SEQUENCE: 15

Xaa Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Gly Leu Ser Ile Leu Asn Arg
            20                  25                  30

Asn Arg Gly Thr Ala Arg Tyr His Thr Arg Leu Ser Phe Thr Ile Met
        35                  40                  45

Leu His Asn Lys Asp Lys Ser Ile Leu Glu Asn Ile Gln Ser Thr Trp
    50                  55                  60

Lys Val Gly Ser Ile Leu Asn Asn Gly Asp His Tyr Val Ser Leu Val
65                  70                  75                  80

Val Tyr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Asn Ile Ser Lys Glu Arg Pro Leu
145                 150                 155                 160
```

```
Ile Asn Lys Asn Ile Pro Asn Phe Lys Trp Leu Ala Gly Phe Thr Ser
            165                 170                 175

Gly Asp Gly Ser Phe Phe Val Arg Leu Arg Lys Ser Asn Val Asn Ala
        180                 185                 190

Arg Val Arg Val Gln Leu Val Phe Glu Ile Ser Gln His Ile Arg Asp
    195                 200                 205

Lys Asn Leu Met Asn Ser Leu Ile Thr Tyr Leu Gly Cys Gly His Ile
210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
            245                 250                 255

Thr Leu Ile Gly Val Lys Leu Glu Asp Phe Glu Asp Trp Cys Lys Val
        260                 265                 270

Ala Lys Leu Ile Glu Glu Lys Lys His Leu Thr Glu Ser Gly Leu Asp
    275                 280                 285

Glu Ile Lys Lys Ile Lys Leu Asn Met Asn Lys Gly Arg
290                 295                 300

<210> SEQ ID NO 16
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 16

Xaa Xaa Xaa Xaa Ser Arg Arg Glu Ser Ile Asn Pro Trp Thr Leu Thr
1               5                   10                  15

Gly Phe Ala Asp Ala Glu Gly Ser Phe Gly Leu Ser Ile Leu Asn Arg
            20                  25                  30

Asn Arg Gly Thr Ala Arg Tyr His Thr Arg Leu Ser Phe Thr Ile Met
        35                  40                  45

Leu His Asn Lys Asp Lys Ser Ile Leu Glu Asn Ile Gln Ser Thr Trp
    50                  55                  60

Lys Val Gly Ser Ile Leu Asn Asn Gly Asp His Tyr Val Ser Leu Val
65                  70                  75                  80

Val Tyr Ala Phe Glu Asp Leu Lys Val Ile Ile Asp His Phe Glu Lys
            85                  90                  95

Tyr Pro Leu Ile Thr Gln Lys Leu Gly Asp Tyr Lys Leu Phe Lys Gln
        100                 105                 110

Ala Phe Ser Val Met Glu Asn Lys Glu His Leu Lys Glu Asn Gly Ile
    115                 120                 125

Lys Glu Leu Val Arg Ile Lys Ala Lys Met Asn Trp Gly Leu Asn Asp
130                 135                 140

Glu Leu Lys Lys Ala Phe Pro Glu Val Ile Ser Arg Glu Arg Pro Leu
145                 150                 155                 160

Ile Asn Lys Asn Ile Pro Asn Gly Lys Trp Leu Ala Gly Phe Thr Ser
            165                 170                 175

Gly Asp Gly Ser Phe Phe Val Arg Leu Arg Lys Ser Asn Val Asn Ala
        180                 185                 190
```

```
Arg Val Arg Val Gln Leu Val Phe Glu Ile Ser Gln His Ile Arg Asp
            195                 200                 205

Lys Asn Leu Met Asn Ser Leu Ile Thr Tyr Leu Gly Cys Gly His Ile
210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
            245                 250                 255

Thr Leu Ile Gly Met Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Arg Arg
            290                 295                 300

<210> SEQ ID NO 17
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 17

Xaa Xaa Xaa Xaa Xaa Xaa Xaa Ser Ile Asn Pro Trp Thr Leu Thr
1               5                   10                  15

Gly Phe Ala Asp Ala Glu Gly Ser Phe Ile Leu Asp Ile Arg Asn Arg
            20                  25                  30

Asn Asn Glu Ser Asn Arg Tyr Arg Thr Ser Leu Arg Phe Gln Ile Thr
        35                  40                  45

Leu His Asn Lys Asp Lys Ser Ile Leu Glu Asn Ile Gln Ser Thr Trp
    50                  55                  60

Lys Val Gly Lys Ile Thr Asn Ser Ser Asp Arg Ala Val Met Leu Arg
65                  70                  75                  80

Val Thr Arg Phe Glu Asp Leu Lys Val Ile Asp His Phe Glu Lys
            85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
            115                 120                 125

Lys Glu Leu Val Arg Ile Lys Ala Lys Met Asn Trp Gly Leu Asn Asp
        130                 135                 140

Glu Leu Lys Lys Ala Phe Pro Glu Val Ile Ser Arg Glu Arg Pro Leu
145                 150                 155                 160

Ile Asn Lys Asn Ile Pro Asn Gly Lys Trp Leu Ala Gly Phe Thr Ala
            165                 170                 175

Gly Asp Gly His Phe Gly Val Asn Leu Lys Lys Val Lys Gly Thr Ala
            180                 185                 190

Lys Val Tyr Val Gly Leu Arg Phe Ala Ile Ser Gln His Ile Arg Asp
            195                 200                 205

Lys Asn Leu Met Asn Ser Leu Ile Thr Tyr Leu Gly Cys Gly Ser Ile
            210                 215                 220

Arg Glu Lys Asn Lys Ser Glu Phe Arg Trp Leu Glu Phe Glu Val Thr
```

```
                225                 230                 235                 240

Lys Phe Ser Asp Ile Asn Asp Lys Ile Ile Pro Val Phe Gln Glu Asn
                245                 250                 255

Thr Leu Ile Gly Met Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Arg Arg
        290                 295                 300

<210> SEQ ID NO 18
<211> LENGTH: 301
<212> TYPE: PRT
<213> ORGANISM: Artificial Sequence
<220> FEATURE:
<223> OTHER INFORMATION: Made in Lab - reprogrammed I-OnuI LHE
      thermostable variant
<220> FEATURE:
<221> NAME/KEY: MOD_RES
<222> LOCATION: (1)..(8)
<223> OTHER INFORMATION: Any amino acid or absent

<400> SEQUENCE: 18

Xaa Xaa Xaa Xaa Xaa Xaa Xaa Xaa Ser Ile Asn Pro Trp Thr Leu Thr
1               5                   10                  15

Gly Phe Ala Asp Ala Glu Gly Cys Phe Arg Leu Asp Ile Arg Asn Ala
            20                  25                  30

Asn Asp Leu Arg Ala Gly Tyr Arg Thr Arg Leu Ala Phe Glu Ile Val
        35                  40                  45

Leu His Asn Lys Asp Lys Ser Ile Leu Glu Asn Ile Gln Ser Thr Trp
    50                  55                  60

Lys Val Gly Thr Ile Tyr Asn Ala Gly Asp Asn Ala Val Arg Leu Gln
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Met Asn Trp Gly Leu Asn Asp
    130                 135                 140

Glu Leu Lys Lys Ala Phe Pro Glu Val Ile Ser Arg Glu Arg Ser Leu
145                 150                 155                 160

Ile Asn Lys Asn Ile Pro Asn Gly Lys Trp Leu Ala Gly Phe Thr Ser
                165                 170                 175

Gly Asp Gly Ser Phe Val Val Glu Leu Lys Lys Arg Arg Ser Pro Val
            180                 185                 190

Lys Val Gly Val Arg Leu Arg Phe Ser Ile Thr Gln His Ile Arg Asp
        195                 200                 205

Lys Asn Leu Met Asn Ser Leu Ile Thr Tyr Leu Gly Cys Gly Arg Ile
    210                 215                 220

Val Glu Asn Asn Lys Ser Glu His Ser Trp Leu Glu Phe Ile Val Thr
225                 230                 235                 240

Lys Phe Ser Asp Ile Asn Asp Lys Ile Ile Pro Val Phe Gln Glu Asn
                245                 250                 255

Thr Leu Ile Gly Met Lys Leu Glu Asp Phe Glu Asp Trp Cys Lys Val
            260                 265                 270
```

```
Ala Lys Leu Ile Glu Glu Lys Lys His Leu Thr Glu Ser Gly Leu Asp
        275                 280                 285

Glu Ile Lys Lys Ile Lys Leu Asn Met Asn Lys Arg Arg
    290                 295                 300
```

<210> SEQ ID NO 19
<211> LENGTH: 1743
<212> TYPE: RNA
<213> ORGANISM: Artificial Sequence
<220> FEATURE:
<223> OTHER INFORMATION: Made in Lab - BCL11A I-OnuI HE variant codon optimized mRNA

<400> SEQUENCE: 19

```
augggaucac cgccuaagaa gaagagaaaa gugucgagaa gggaaucaau uaacccuugg      60
auccugaccg gcuucgccga cgccgagggg ucauuccucc uccgcauucg caauaauaac     120
aagaguagcg uaggcuacuc uacgagcug gcuuccaga uuaccuccca caacaaggac      180
aagaguaucc uggaaaacau ccagucgacu uggaaggugg gcguaauagc uaacagugga     240
gacaacgcug ugucacucaa agucaccagg uucgaggacc ugaaggugau cauugaccac     300
uucgagaagu acccacugau cacucagaag cugguugacu acaagcuguu caagcaagca     360
uuuucgguga uggagaacaa agagcaccug aaggaaaaug gaauuaagga acuugugcgc     420
aucaaggcca guugaacug gggacuuacg gaugagcuca gaaagcguu uccugaaaac      480
aucucgaaag agaggagucu gauuaacaag aauaucccua acuucaagug gcuggccggg     540
uucacguccg gggaaggaug cuuuucguc aaccucauaa aaagcaaguc uaaacuugga      600
gugcaagugc agcugguguu ucaaucacu caacacauca aagacaagaa ccucaugaac      660
ucgcucauca ccuaccuggg uugcggauau acaaagaga aaaacaaguc agaauuuucc      720
uggcuggauu ucgugugac aaaguucagc gacaucaacg acaagaucau cccgguguuc     780
caggagaaca cccucaucgg cgugaagcug gaggacuucg aagauggug caagguggcg     840
aagcuuaucg aagaaagaa gcaccugacc gaguccggac uggacgagau caagaagauc     900
aaacugaaca ugaacaaggg ccggagauau ccauacgaug ucccagauua ugcgcucgag     960
aguggggaag gucgcggcuc cuugcucacc guggggaug ucgaagaaaa cccaggucuu    1020
gcuagcguga gcaaggggcga ggagcuguuc accggggugg ugcccauccu ggucgagcug    1080
gacggcgacg uaaacggcca caguucagc guguccggcg agggcgaggg cgaugccacc    1140
uacggcaagc ugacccugaa guucaucugc caccggca agcugcccgu gccuggccc     1200
acccucguga ccacccugac cuacggcgug caggcuuca gccgcuaccc cgaccacaug    1260
aagcagcacg acuucuucaa guccgccaug cccgaaggcu acguccagga gcgcaccauc    1320
uucuucaagg acgacggcaa cuacaagacc cgcgccgagg ugaaguucga gggcgacacc    1380
cuggugaacc gcaucgagcu gaagggcauc gacuucaagg aggacggcaa cauccugggg    1440
cacaagcugg aguacaacua caacagccac aacgucuaua ucauggccga caagcagaag    1500
aacggcauca gguggaacuu caagauccgc cacaacaucg aggacggcag cgucagcuc    1560
gccgaccacu accagcagaa caccccauc ggcgacggcc ccgucugcu gcccgacaac    1620
cacuaccuga gcacccaguc cgcccugagc aaagacccca cgagaagcg cgaucacaug    1680
guccugcugg aguucgugac cgccgccggg aucacucucg gcauggacga gcuguacaag    1740
uga                                                                 1743
```

<210> SEQ ID NO 20
<211> LENGTH: 1743
<212> TYPE: RNA
<213> ORGANISM: Artificial Sequence
<220> FEATURE:
<223> OTHER INFORMATION: Made in Lab - BCL11A I-OnuI HE variant mRNA

<400> SEQUENCE: 20

```
augggaucac cgccuaagaa gaagagaaaa gugucgagaa gggaauccau caacccaugg     60
auucugacug guuucgcuga ugccgaagga agcuucgugc uaaguaucca aaacagaaac    120
gauuaugcua cugguuacag aauucaccug acauuccaaa ucacccugca caacaaggac    180
aaaucgauuc uggagaauau ccagucgacu uggaaggucg gcaaaaucaa uaacacgggc    240
gacaaccucg uccaacugag agcuaccgu uucgaagauu ugaaagugau uaucgaccac    300
uucgagaaau auccgcugau aacacagaaa uugggcgauu acaaguuguu aaacaggca    360
uucagcguca uggagaacaa agaacaucuu aaggagaaug ggauuaagga gcucguacga    420
aucaaagcua agaugaauug gggucucaau gacgaauuga aaaaagcauu uccagagaac    480
auuagcaaag agcgcccccu uaucaauaag aacauuccga auucaaaug gcuggcugga    540
uucacaucug ugauggcuc cuucuucgug cgccuaagaa agucuaaugu uaaugcuaga    600
guacgugugc aacugguauu cgagaucuca cagcacauca gagacaagaa ccugaugaau    660
ucauugauaa cauaccuagg cuguggcac aucuacgagg gaaacaaauc ugagcgcagu    720
uggcuccaau ucagaguaga aaaauucagc gauaucaacg acaagaucau uccgguauuc    780
caggaaaaua cucugauugg cgucaaacuc gaggacuuug aagauuggug caagguugcc    840
aaauugaucg aagagaagaa acaccugacc gaauccgguu uggaugagau uaagaaaauc    900
agcugaaca ugaacaaagg ucuagauau ccaucgaug ucccagauua ugcgcucgag    960
aguggggaag gucgcggcuc cuugcucacc gugggggaug ucgaagaaaa cccagguccc   1020
gcuagcguga gcaagggcga ggagcuguuc accggggugg ugcccauccu ggucgagcug   1080
gacggcgacg uaaacggcca caaguucagc gugucggcg agggcgaggg cgaugccacc   1140
uacggcaagc ugacccugaa guucaucugc accaccggca agcugcccgu gccuggccc   1200
acccucguga ccacccugac cuacggcgug cagugcuuca gccgcuaccc cgaccacaug   1260
aagcagcacg acuucuucaa guccgccaug cccgaaggcu acguccagga gcgcaccauc   1320
uucuucaagg acgacggcaa cuacaagacc cgcgccgagg ugaaguucga gggcgacacc   1380
cugguagaacc gcaucgagcu gaagggcauc gacuucaagg aggacggcaa cauccugggg   1440
cacaagcugg aguacaacua caacagccac aacgucuaua ucauggccga caagcagaag   1500
aacggcauca agguggaacuu caagauccgc cacaacaucg aggacggcag cgugcagcuc   1560
gccgaccacu accagcagaa cacccccauc ggcgacggcc ccgugcugcu gcccgacaac   1620
cacuaccuga gcacccaguc cgcccugagc aaagacccca acgagaagcg cgaucacaug   1680
guccugcugg aguucgugac cgccgccggg aucacucucg gcauggacga gcuguacaag   1740
uga                                                                 1743
```

<210> SEQ ID NO 21
<211> LENGTH: 1743
<212> TYPE: RNA
<213> ORGANISM: Artificial Sequence
<220> FEATURE:
<223> OTHER INFORMATION: Made in Lab - BCL11A I-OnuI HE A5 variant mRNA

<400> SEQUENCE: 21

-continued

| | |
|---|---|
| augggaucac cgccuaagaa gaagagaaaa gugucgagaa gggaauccau caacccaugg | 60 |
| acucugacug guuucgcuga ugccgaagga agcuucgugc uaaguaucca aaacagaaac | 120 |
| gauuaugcua cugguuacag aauucaccug acauuccaaa ucacccugca aacaaggac | 180 |
| aaaucgauuc uggagaauau ccagucgacu uggaaggucg gcaaaaucaa uaacacgggc | 240 |
| gacaaccucg uccaacugag agucuaccgu uucgaagauu ugaaagugau uaucgaccac | 300 |
| uucgagaaau auccgcugau aacacagaaa uugggcgauu acaaauuguu uaaacaggca | 360 |
| uucagcguca uggagaacaa agaacaucuu aaggagaaug ggauuaagga gcucguacga | 420 |
| aucaaagcua agaugaauug gggucucaau gacgaauuga aaaaagcauu uccagaggug | 480 |
| auuagcaggg agcgcccccu uaucaauaag aacauuccga augggaaaug gcuggcugga | 540 |
| uucacaucug gugauggcuc cuucuucgug cgccuaagaa agucuaaugu uaaugcuaga | 600 |
| guacgugugc aacugguauu cgagaucuca cagcacauca gagauaagaa ccugaugaau | 660 |
| ucauugauaa cauaccuagg cuguggucac aucuacgagg gaaacaaauc ugagcgcucu | 720 |
| uggcuccaau ucagaguaga aaaauucagc gauaucaaug acaagaucau uccgguauuc | 780 |
| caggaaaaua cucugauugg caugaaacuc gaggacuuug aagauuggug caagguugcc | 840 |
| aaauugaucg aagagaagaa acaccugacc gaauccgguu uggaugagau uaagaaaauc | 900 |
| aagcugaaca ugaacaaaag acguagauau ccaucgaug ucccagauua ugcgcucgag | 960 |
| aguggggaag gucgcggcuc cuugcucacc uguggggaug ucgaagaaaa cccaggcccc | 1020 |
| gcuagcguga gcaagggcga ggagcuguuc accggggugg ugcccauccu ggucgagcug | 1080 |
| gacggcgacg uaaacggcca caaguucagc gugcccggcg agggcgaggg cgaugccacc | 1140 |
| uacggcaagc ugacccugaa guucaucugc accaccggca agcugcccgu gcccuggccc | 1200 |
| acccucguga ccacccugac cuacggcgug cagugcuuca gccgcuaccc cgaccacaug | 1260 |
| aagcagcacg acuucuucaa guccgccaug cccgaaggcu acguccagga gcgcaccauc | 1320 |
| uucuucaagg acgacggcaa cuacaagacc cgcgccgagg ugaaguucga gggcgacacc | 1380 |
| cugguggaacc gcaucgagcu gaagggcauc gacuucaagg aggacggcaa cauccugggg | 1440 |
| cacaagcugg aguacaacua caacagccac aacgucuaua ucauggccga caagcagaag | 1500 |
| aacggcauca aggugaacuu caagauccgc cacaacaucg aggacggcag cgugcagcuc | 1560 |
| gccgaccacu accagcagaa cacccccauc ggcgacggcc ccgugcugcu gcccgacaac | 1620 |
| cacuaccuga gcacccaguc cgcccugagc aaagacccca acgagaagcg cgaucacaug | 1680 |
| guccugcugg aguucgugac cgccgccggg aucacucucg gcauggacga gcuguacaag | 1740 |
| uga | 1743 |

<210> SEQ ID NO 22
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL

<400> SEQUENCE: 22

Met Gly Ser Cys Arg Pro Pro Lys Lys Lys Arg Lys Val Val Asp Leu
1               5                   10                  15

Arg Thr Leu Gly Tyr Ser Gln Gln Gln Gln Glu Lys Ile Lys Pro Lys
            20                  25                  30

Val Arg Ser Thr Val Ala Gln His His Glu Ala Leu Val Gly His Gly
        35                  40                  45

```
Phe Thr His Ala His Ile Val Ala Leu Ser Gln His Pro Ala Ala Leu
 50                  55                  60

Gly Thr Val Ala Val Thr Tyr Gln His Ile Ile Thr Ala Leu Pro Glu
 65                  70                  75                  80

Ala Thr His Glu Asp Ile Val Gly Val Gly Lys Gln Trp Ser Gly Ala
                 85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
            115                 120                 125

Gly Val Thr Ala Met Glu Ala Val His Ala Ser Arg Asn Ala Leu Thr
130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
            195                 200                 205

Leu Pro Val Leu Cys Gln Asp His Gly Leu Thr Pro Asp Gln Val Val
            210                 215                 220

Ala Ile Ala Ser Asn Gly Gly Lys Gln Ala Leu Glu Thr Val Gln
225                 230                 235                 240

Arg Leu Leu Pro Val Leu Cys Gln Asp His Gly Leu Thr Pro Asp Gln
                245                 250                 255

Val Val Ala Ile Ala Ser Asn Asn Gly Gly Lys Gln Ala Leu Glu Thr
            260                 265                 270

Val Gln Arg Leu Leu Pro Val Leu Cys Gln Asp His Gly Leu Thr Pro
            275                 280                 285

Asp Gln Val Val Ala Ile Ala Ser Asn Asn Gly Gly Lys Gln Ala Leu
            290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser Asn Asn Gly Gly Lys Gln
                325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser Asn Asn Gly Gly
            355                 360                 365

Lys Gln Ala Leu Glu Thr Val Gln Arg Leu Leu Pro Val Leu Cys Gln
            370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
            420                 425                 430

Asn Gly Gly Gly Lys Gln Ala Leu Glu Thr Val Gln Arg Leu Leu Pro
            435                 440                 445

Val Leu Cys Gln Asp His Gly Leu Thr Pro Asp Gln Val Val Ala Ile
450                 455                 460

Ala Ser Asn Asn Gly Gly Lys Gln Ala Leu Glu Thr Val Gln Arg Leu
```

-continued

```
            465                 470                 475                 480
        Leu Pro Val Leu Cys Gln Asp His Gly Leu Thr Pro Asp Gln Val Val
                        485                 490                 495
        Ala Ile Ala Ser His Asp Gly Gly Lys Gln Ala Leu Glu Thr Val Gln
                        500                 505                 510
        Arg Leu Leu Pro Val Leu Cys Gln Asp His Gly Leu Thr Pro Asp Gln
                        515                 520                 525
        Val Val Ala Ile Ala Ser Asn Gly Gly Lys Gln Ala Leu Glu Thr
                        530                 535                 540
        Val Gln Arg Leu Leu Pro Val Leu Cys Gln Asp His Gly Leu Thr Pro
        545                 550                 555                 560
        Asp Gln Val Val Ala Ile Ala Ser His Asp Gly Gly Lys Gln Ala Leu
                                565                 570                 575
        Glu Ser Ile Val Ala Gln Leu Ser Arg Pro Asp Pro Ala Leu Ala Ala
                        580                 585                 590
        Leu Thr Asn Asp His Leu Val Ala Leu Ala Cys Leu Gly Gly Arg Pro
                        595                 600                 605
        Ala Met Asp Ala Val Lys Lys Gly Leu Pro His Ala Pro Glu Leu Ile
                        610                 615                 620
        Arg Arg Val Asn Arg Arg Ile Gly Glu Arg Thr Ser His Arg Val Ala
        625                 630                 635                 640
        Ile Ser Arg Val Gly Gly Ser Arg Arg Glu Ser Ile Asn Pro Trp
                        645                 650                 655
        Ile Leu Thr Gly Phe Ala Asp Ala Glu Gly Ser Phe Gly Leu Ser Ile
                        660                 665                 670
        Leu Asn Arg Asn Arg Gly Thr Ala Arg Tyr His Thr Arg Leu Ser Phe
                        675                 680                 685
        Thr Ile Met Leu His Asn Lys Asp Lys Ser Ile Leu Glu Asn Ile Gln
                        690                 695                 700
        Ser Thr Trp Lys Val Gly Ser Ile Leu Asn Asn Gly Asp His Tyr Val
        705                 710                 715                 720
        Ser Leu Val Val Tyr Arg Phe Glu Asp Leu Lys Val Ile Ile Asp His
                        725                 730                 735
        Phe Glu Lys Tyr Pro Leu Ile Thr Gln Lys Leu Gly Asp Tyr Lys Leu
                        740                 745                 750
        Phe Lys Gln Ala Phe Ser Val Met Glu Asn Lys Glu His Leu Lys Glu
                        755                 760                 765
        Asn Gly Ile Lys Glu Leu Val Arg Ile Lys Ala Lys Met Asn Trp Gly
                        770                 775                 780
        Leu Asn Asp Glu Leu Lys Lys Ala Phe Pro Glu Asn Ile Ser Lys Glu
        785                 790                 795                 800
        Arg Pro Leu Ile Asn Lys Asn Ile Pro Asn Phe Lys Trp Leu Ala Gly
                        805                 810                 815
        Phe Thr Ser Gly Asp Gly Ser Phe Phe Val Arg Leu Arg Lys Ser Asn
                        820                 825                 830
        Val Asn Ala Arg Val Arg Val Gln Leu Val Phe Glu Ile Ser Gln His
                        835                 840                 845
        Ile Arg Asp Lys Asn Leu Met Asn Ser Leu Ile Thr Tyr Leu Gly Cys
                        850                 855                 860
        Gly His Ile Tyr Glu Gly Asn Lys Ser Glu Arg Ser Trp Leu Gln Phe
        865                 870                 875                 880
        Arg Val Glu Lys Phe Ser Asp Ile Asn Asp Lys Ile Ile Pro Val Phe
                        885                 890                 895
```

```
Gln Glu Asn Thr Leu Ile Gly Val Lys Leu Glu Asp Phe Glu Asp Trp
                900                 905                 910
Cys Lys Val Ala Lys Leu Ile Glu Glu Lys Lys His Leu Thr Glu Ser
                915                 920                 925
Gly Leu Asp Glu Ile Lys Lys Ile Lys Leu Asn Met Asn Lys Gly Arg
                930                 935                 940

<210> SEQ ID NO 23
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL

<400> SEQUENCE: 23

Met Gly Ser Cys Arg Pro Pro Lys Lys Lys Arg Lys Val Val Asp Leu
1               5                   10                  15
Arg Thr Leu Gly Tyr Ser Gln Gln Gln Glu Lys Ile Lys Pro Lys
                20                  25                  30
Val Arg Ser Thr Val Ala Gln His His Glu Ala Leu Val Gly His Gly
                35                  40                  45
Phe Thr His Ala His Ile Val Ala Leu Ser Gln His Pro Ala Ala Leu
            50                  55                  60
Gly Thr Val Ala Val Thr Tyr Gln His Ile Ile Thr Ala Leu Pro Glu
65                  70                  75                  80
Ala Thr His Glu Asp Ile Val Gly Val Gly Lys Gln Trp Ser Gly Ala
                85                  90                  95
Arg Ala Leu Glu Ala Leu Leu Thr Asp Ala Gly Glu Leu Arg Gly Pro
                100                 105                 110
Pro Leu Gln Leu Asp Thr Gly Gln Leu Val Lys Ile Ala Lys Arg Gly
                115                 120                 125
Gly Val Thr Ala Met Glu Ala Val His Ala Ser Arg Asn Ala Leu Thr
            130                 135                 140
Gly Ala Pro Leu Asn Leu Thr Pro Asp Gln Val Val Ala Ile Ala Ser
145                 150                 155                 160
Asn Asn Gly Gly Lys Gln Ala Leu Glu Thr Val Gln Arg Leu Leu Pro
                165                 170                 175
Val Leu Cys Gln Asp His Gly Leu Thr Pro Asp Gln Val Val Ala Ile
                180                 185                 190
Ala Ser Asn Asn Gly Gly Lys Gln Ala Leu Glu Thr Val Gln Arg Leu
                195                 200                 205
Leu Pro Val Leu Cys Gln Asp His Gly Leu Thr Pro Asp Gln Val Val
            210                 215                 220
Ala Ile Ala Ser Asn Gly Gly Gly Lys Gln Ala Leu Glu Thr Val Gln
225                 230                 235                 240
Arg Leu Leu Pro Val Leu Cys Gln Asp His Gly Leu Thr Pro Asp Gln
                245                 250                 255
Val Val Ala Ile Ala Ser Asn Asn Gly Gly Lys Gln Ala Leu Glu Thr
                260                 265                 270
Val Gln Arg Leu Leu Pro Val Leu Cys Gln Asp His Gly Leu Thr Pro
                275                 280                 285
Asp Gln Val Val Ala Ile Ala Ser Asn Asn Gly Gly Lys Gln Ala Leu
            290                 295                 300
Glu Thr Val Gln Arg Leu Leu Pro Val Leu Cys Gln Asp His Gly Leu
305                 310                 315                 320
```

```
Thr Pro Asp Gln Val Val Ala Ile Ala Ser Asn Asn Gly Lys Gln
            325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser Asn Asn Gly Gly
            355                 360                 365

Lys Gln Ala Leu Glu Thr Val Gln Arg Leu Leu Pro Val Leu Cys Gln
370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
                420                 425                 430

Asn Gly Gly Gly Lys Gln Ala Leu Glu Thr Val Gln Arg Leu Leu Pro
            435                 440                 445

Val Leu Cys Gln Asp His Gly Leu Thr Pro Asp Gln Val Val Ala Ile
            450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
                485                 490                 495

Ala Ile Ala Ser His Asp Gly Gly Lys Gln Ala Leu Glu Thr Val Gln
                500                 505                 510

Arg Leu Leu Pro Val Leu Cys Gln Asp His Gly Leu Thr Pro Asp Gln
                515                 520                 525

Val Val Ala Ile Ala Ser Asn Gly Gly Gly Lys Gln Ala Leu Glu Thr
            530                 535                 540

Val Gln Arg Leu Leu Pro Val Leu Cys Gln Asp His Gly Leu Thr Pro
545                 550                 555                 560

Asp Gln Val Val Ala Ile Ala Ser His Asp Gly Gly Lys Gln Ala Leu
                565                 570                 575

Glu Ser Ile Val Ala Gln Leu Ser Arg Pro Asp Pro Ala Leu Ala Ala
            580                 585                 590

Leu Thr Asn Asp His Leu Val Ala Leu Ala Cys Leu Gly Gly Arg Pro
            595                 600                 605

Ala Met Asp Ala Val Lys Lys Gly Leu Pro His Ala Pro Glu Leu Ile
            610                 615                 620

Arg Arg Val Asn Arg Arg Ile Gly Glu Arg Thr Ser His Arg Val Ala
625                 630                 635                 640

Ile Ser Arg Val Gly Gly Ser Ser Arg Arg Glu Ser Ile Asn Pro Trp
                645                 650                 655

Thr Leu Thr Gly Phe Ala Asp Ala Glu Gly Ser Phe Gly Leu Ser Ile
                660                 665                 670

Leu Asn Arg Asn Arg Gly Thr Ala Arg Tyr His Thr Arg Leu Ser Phe
            675                 680                 685

Thr Ile Met Leu His Asn Lys Asp Lys Ser Ile Leu Glu Asn Ile Gln
            690                 695                 700

Ser Thr Trp Lys Val Gly Ser Ile Leu Asn Asn Gly Asp His Tyr Val
705                 710                 715                 720

Ser Leu Val Val Tyr Ala Phe Glu Asp Leu Lys Val Ile Ile Asp His
                725                 730                 735
```

```
Phe Glu Lys Tyr Pro Leu Ile Thr Gln Lys Leu Gly Asp Tyr Lys Leu
                740                 745                 750

Phe Lys Gln Ala Phe Ser Val Met Glu Asn Lys Glu His Leu Lys Glu
            755                 760                 765

Asn Gly Ile Lys Glu Leu Val Arg Ile Lys Ala Lys Met Asn Trp Gly
        770                 775                 780

Leu Asn Asp Glu Leu Lys Lys Ala Phe Pro Glu Val Ile Ser Arg Glu
785                 790                 795                 800

Arg Pro Leu Ile Asn Lys Asn Ile Pro Asn Gly Lys Trp Leu Ala Gly
                805                 810                 815

Phe Thr Ser Gly Asp Gly Ser Phe Phe Val Arg Leu Arg Lys Ser Asn
            820                 825                 830

Val Asn Ala Arg Val Arg Val Gln Leu Val Phe Glu Ile Ser Gln His
        835                 840                 845

Ile Arg Asp Lys Asn Leu Met Asn Ser Leu Ile Thr Tyr Leu Gly Cys
    850                 855                 860

Gly His Ile Tyr Glu Gly Asn Lys Ser Glu Arg Ser Trp Leu Gln Phe
865                 870                 875                 880

Arg Val Glu Lys Phe Ser Asp Ile Asn Asp Lys Ile Ile Pro Val Phe
                885                 890                 895

Gln Glu Asn Thr Leu Ile Gly Met Lys Leu Glu Asp Phe Glu Asp Trp
            900                 905                 910

Cys Lys Val Ala Lys Leu Ile Glu Lys Lys His Leu Thr Glu Ser
        915                 920                 925

Gly Leu Asp Glu Ile Lys Lys Ile Lys Leu Asn Met Asn Lys Arg Arg
    930                 935                 940

<210> SEQ ID NO 24
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 24

Gly Gly Gly
1

<210> SEQ ID NO 25
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 25

Asp Gly Gly Gly Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 26

Thr Gly Glu Lys Pro
1               5
```

```
<210> SEQ ID NO 27
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 27

Gly Gly Arg Arg
1

<210> SEQ ID NO 28
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 28

Gly Gly Gly Gly Ser
1               5

<210> SEQ ID NO 29
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 29

Glu Gly Lys Ser Ser Gly Ser Gly Ser Glu Ser Lys Val Asp
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 30

Lys Glu Ser Gly Ser Val Ser Ser Glu Gln Leu Ala Gln Phe Arg Ser
1               5                   10                  15

Leu Asp

<210> SEQ ID NO 31
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 31

Gly Gly Arg Arg Gly Gly Gly Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 32

Leu Arg Gln Arg Asp Gly Glu Arg Pro
1               5
```

```
<210> SEQ ID NO 33
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 33

Leu Arg Gln Lys Asp Gly Gly Gly Ser Glu Arg Pro
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 34

Leu Arg Gln Lys Asp Gly Gly Gly Ser Gly Gly Gly Ser Glu Arg Pro
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 35

Glu Xaa Xaa Tyr Xaa Gln Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 36

Glu Asn Leu Tyr Phe Gln Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 37

Glu Asn Leu Tyr Phe Gln Ser
1               5

<210> SEQ ID NO 38
```

```
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 39
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 39

Ala Thr Asn Phe Ser Leu Leu Lys Gln Ala Gly Asp Val Glu Glu Asn
1               5                   10                  15

Pro Gly Pro

<210> SEQ ID NO 40
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Leu Leu Lys Gln Ala Gly Asp Val Glu Glu Asn Pro Gly Pro
1               5                   10

<210> SEQ ID NO 41
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 42
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 42

Glu Gly Arg Gly Ser Leu Leu Thr Cys Gly Asp Val Glu Glu Asn Pro
1               5                   10                  15

Gly Pro

<210> SEQ ID NO 43
<211> LENGTH: 13
<212> TYPE: PRT
<213> ORGANISM: Artificial Sequence
<220> FEATURE:
```

```
<223> OTHER INFORMATION: Self-cleaving polypeptide comprising 2A site

<400> SEQUENCE: 43

Leu Leu Thr Cys Gly Asp Val Glu Glu Asn Pro Gly Pro
1               5                   10

<210> SEQ ID NO 44
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 44

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 45
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 45

Gln Cys Thr Asn Tyr Ala Leu Leu Lys Leu Ala Gly Asp Val Glu Ser
1               5                   10                  15

Asn Pro Gly Pro
            20

<210> SEQ ID NO 46
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 46

Leu Leu Lys Leu Ala Gly Asp Val Glu Ser Asn Pro Gly Pro
1               5                   10

<210> SEQ ID NO 47
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 47

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 48
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 48

Val Lys Gln Thr Leu Asn Phe Asp Leu Leu Lys Leu Ala Gly Asp Val
```

```
1               5                   10                  15

Glu Ser Asn Pro Gly Pro
            20

<210> SEQ ID NO 49
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 49

Leu Leu Lys Leu Ala Gly Asp Val Glu Ser Asn Pro Gly Pro
1               5                   10

<210> SEQ ID NO 50
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 50

Leu Leu Asn Phe Asp Leu Leu Lys Leu Ala Gly Asp Val Glu Ser Asn
1               5                   10                  15

Pro Gly Pro

<210> SEQ ID NO 51
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 51

Thr Leu Asn Phe Asp Leu Leu Lys Leu Ala Gly Asp Val Glu Ser Asn
1               5                   10                  15

Pro Gly Pro

<210> SEQ ID NO 52
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 52

Leu Leu Lys Leu Ala Gly Asp Val Glu Ser Asn Pro Gly Pro
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 53

Asn Phe Asp Leu Leu Lys Leu Ala Gly Asp Val Glu Ser Asn Pro Gly
1               5                   10                  15

Pro

<210> SEQ ID NO 54
<211> LENGTH: 20
```

```
<212> TYPE: PRT
<213> ORGANISM: Artificial Sequence
<220> FEATURE:
<223> OTHER INFORMATION: Self-cleaving polypeptide comprising 2A site

<400> SEQUENCE: 54

Gln Leu Leu Asn Phe Asp Leu Leu Lys Leu Ala Gly Asp Val Glu Ser
1               5                   10                  15

Asn Pro Gly Pro
            20

<210> SEQ ID NO 55
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 56
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 57
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 57

Leu Asn Phe Asp Leu Leu Lys Leu Ala Gly Asp Val Glu Ser Asn Pro
1               5                   10                  15

Gly Pro

<210> SEQ ID NO 58
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 58

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30
```

```
Asp Val Glu Ser Asn Pro Gly Pro
        35                  40

<210> SEQ ID NO 59
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 59

Glu Ala Arg His Lys Gln Lys Ile Val Ala Pro Val Lys Gln Thr Leu
1                5                   10                  15

Asn Phe Asp Leu Leu Lys Leu Ala Gly Asp Val Glu Ser Asn Pro Gly
            20                  25                  30

Pro
```